(12) United States Patent
Dorsch et al.

(10) Patent No.: US 9,051,318 B2
(45) Date of Patent: Jun. 9, 2015

(54) PYRIDO [2, 3-B] PYRAZINE COMPOUNDS AND THEIR THERAPEUTICAL USES SUCH AS FOR INHIBITING ATP CONSUMING PROTEINS AND TREATING DISEASES ASSOCIATED THEREWITH

(75) Inventors: Dieter Dorsch, Ober-Ramstadt (DE); Alfred Jonczyk, Darmstadt (DE); Guenter Hoelzemann, Seeheim-Jugenheim (DE); Christiane Amendt, Muehltal/Trautheim (DE); Frank Zenke, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 10 days.

(21) Appl. No.: 14/002,991

(22) PCT Filed: Feb. 13, 2012

(86) PCT No.: PCT/EP2012/000630
§ 371 (c)(1),
(2), (4) Date: Sep. 4, 2013

(87) PCT Pub. No.: WO2012/119690
PCT Pub. Date: Sep. 13, 2012

(65) Prior Publication Data
US 2013/0345227 A1    Dec. 26, 2013

(30) Foreign Application Priority Data
Mar. 9, 2011    (EP) .................................. 11001944

(51) Int. Cl.
*A61K 31/4985*    (2006.01)
*C07D 471/04*    (2006.01)
*A61K 45/06*    (2006.01)
*C07D 491/048*    (2006.01)

(52) U.S. Cl.
CPC .......... *C07D 471/04* (2013.01); *A61K 31/4985* (2013.01); *A61K 45/06* (2013.01); *C07D 491/048* (2013.01)

(58) Field of Classification Search
CPC .......................... A61K 31/4985; C07D 471/04

USPC .......... 514/249; 544/350; 546/113, 115, 122, 546/148, 210, 268.1; 548/373.1
See application file for complete search history.

(56) References Cited

U.S. PATENT DOCUMENTS
2011/0288090 A1    11/2011    Armstrong et al.

FOREIGN PATENT DOCUMENTS
CA    2829287    *    9/2012
WO    2010088177 A1    8/2010

OTHER PUBLICATIONS
Jordan, V. C. Nature Reviews: Drug Discovery, 2, 2003, 205.*
Vippagunta, et al. Advanced Drug Delivery Reviews, 48, 2001, 18.*
Hackam, et al. JAMA, 296(14), 2006, 1731-1732.*
International Search Report from PCT/EP2012/000630 dated Mar. 28, 2012.

* cited by examiner

*Primary Examiner* — Douglas M Willis
(74) *Attorney, Agent, or Firm* — Millen, White, Zelano & Branigan, P.C.

(57) ABSTRACT

The present invention relates to novel pyrido[2,3-b]pyrazine compounds of formula (I):

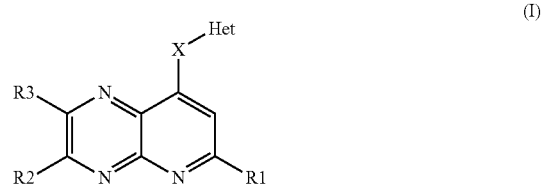

and to the use of such compounds in which the inhibition, regulation and/or modulation of signal transduction by ATP consuming proteins like kinases plays a role, particularly to inhibitors of TGF-beta receptor kinases, and to the use of such compounds for the treatment of kinase-induced diseases, in particular for the treatment of tumors.

19 Claims, No Drawings

PYRIDO [2, 3-B] PYRAZINE COMPOUNDS AND THEIR THERAPEUTICAL USES SUCH AS FOR INHIBITING ATP CONSUMING PROTEINS AND TREATING DISEASES ASSOCIATED THEREWITH

TECHNICAL FIELD

The present invention relates to novel pyrido[2,3-b]pyrazine derivatives and to the use of such compounds in which the inhibition, regulation and/or modulation of signal transduction by ATP consuming proteins like kinases plays a role, particularly to inhibitors of TGF-beta receptor kinases, and to the use of the compounds for the treatment of kinase-induced diseases.

PRIOR ART

Proteins which bind ATP and utilize its energy to change conformation, to phosphorylate substrates, and to initiate signaling cascades are known from many classes, like kinases, phosphatases, chaperones or isomerases. With specific tools and techniques ATP-binding proteins can be enriched.

From the large family of protein kinases, split into subfamilies of tyrosine kinases and serine threonine kinases, a partial list includes cAbl, Akt, ALK, ALK1 and its family members like ALK1 and ALK5, Axl, Aurora A and B, Btk, Dyrk2, EGFR, Erk, Ephrin receptors like EphA2, FAK, FGF receptors like FGFR3, insulin receptor IR and insulin like growth factor receptor IGF1R, IKK2, Jak2, JNK3, cKit, LimK, VEGF receptors 1, 2, and 3, Mek1, Met, P70s6K, PDGFR, PDK1, PI3K, Plk1, PKD1, bRaf, RSK1, Src and its family members, TAK1, Trk A, B, C, Zap70. The different kinases can be described under several synonyms, well known to the one skilled in the art and accessible in data bases like Kinweb to find a gene and protein report with alternative names, classification, gene annotation, sequence and gene structure, and links to the pdb 3D structure information. Similarly, proteomics server will give access to a lot of information and analysis and prediction tools for genes and proteins, including kinases.

As a mechanistic part of the hallmarks of cancer, Ser/Thr kinases and receptor tyrosine kinases (RTK) are phosphorylating enzymes essential in cellular signaling. Cell cycle, survival, proliferation and cell death are cellular processes, regulated by cell signaling, to permit tissue to grow, to regenerate and to be in homeostasis, or to regress. Some kinases are therefore exquisite targets for mammalian therapy.

Of the different families of kinases, which are part of the human kinome the receptor tyrosine kinase KDR, also called VEGF receptor 2, can stimulate endothelial cell survival and proliferation if ligated extra cellular by VEGF. Ligand binding can then lead to intracellular phosphorylation events, a signaling cascade and ultimately to proliferation. Inhibition of this KDR signaling is attempted by various therapies.

Other kinases and ligands important for function of endothelial cells are TIE2 kinase and the angiopoietins, PDGF receptor and PDGF as well as PlGF. Ephrin receptor kinase and ephrins, especially EphB4 and ephrin-B2. In addition, the ligand TGFβ and its receptors TGFβR, i.e. Alk1/Alk5 play an important role in maintenance of vascular integrity. By binding to the TGFβ type II receptor TGFβ can activate 2 distinct type I receptors in endothelial cells, i.e. the EC-restricted ALK1 and the broadly expressed ALK5 with opposite effects on EC behavior. ALK1 stimulates EC proliferation and migration via Smad1/5 transcription factors, ALK5 inhibits those functions via Smad2/3 transcription factors. One example for an Alk5 kinase inhibitor that facilitates EC proliferation and sheet formation is SB-431542. Ligand binding inhibition might be an additional approach to modulate TGFβ receptor signaling also in angiogenesis. This was shown with 2 peptides and also discussed for soluble TGFβ receptors TβR-Fc. Use of anti-TGFβ antibodies, even a TGFβ trap, would be another strategy to inhibit TGFβ signaling.

The TGFβ proteins comprise a family of conserved dimeric proteins with a molecular weight of ~25 kDa, which are ubiquitously expressed and secreted in an inactive form. Local proteolysis in response to appropriate stimuli leads to active TGFβ ligands. TGFβ signaling is implicated in numerous conditions and diseases, including cancer, cardiovascular, bone, CNS, PNS, inflammatory and neurodegenerative disorders.

In epithelial cells, TGFβ inhibits cell proliferation. The transition of normal epithelial cell into carcinoma cells is accompanied by down-regulation of the growth-inhibition response to TGFβ, allowing the cells to escape the autocrine tumor suppressor activities of TGFβ signaling. The increased production of TGFβ by carcinoma cells contributes to the invasive and metastatic behavior of the cancer cells. TGFβ can induce an epithelial-to-mesenchymal transition (EMT) that allows the cells to become invasive and migratory. In addition, the increased TGFβ production exerts effects on stromal and immune cells to provide a favorable microenvironment for cancer progression. TGFβ proteins signal through TβR-I/II receptor kinases and their Smad substrates, but can also signal independent of Smads, such as ERK MAP kinases, PI3 kinase, Rho-like GTPases, protein phosphatase 2A, and Par6. Activated type I TβR kinases enhance survival of cells and can accelerate pathological cell progression.

TGFβ receptor type I and II (TβR I, TβR II) are single-pass transmembrane-spanning intracellular serine/threonine kinases presenting extracellular ligand (TGFβ) binding receptors. Intra-cellular signaling proceeds via auto-phosphorylation, trans-phosphorylation and substrate phosphorylation, leading to modulation of target gene expression. Cloning and genomic organization of TβR proteins is well-known. TβR sequences are deposited in www.uniprot.org as TGFR1_human with accession number P36897, and as TGFβR2_human with accession number P37173. On protein level, type I TβR is described to contain a region rich in Gly and Ser (GS domain) preceeding the receptor kinase domain. TβR II is in its auto/phosphorylated state a constitutively active kinase which binds to the type I receptor and phosphorylates it in the GS domain.

TβReceptor, a ligand TGFβ-bound (activated) tetrameric complex of 2 TβR I and 2 TβR II units, is able to phosphorylate Smads (Smad 2 and Smad 3) in their C-terminal SSXS motifs as substrates which in turn are bound to/by Smad4 to be translocated to the cell nucleus, where they modulate TGFβ responsive genes. The different domains which regulate homomeric and heteromeric complex formation among type I and type II TβRs are known. Mutations in the GS domain of TβR I can be constitutively activating. Kinase inactivating mutation were found with K232R for type I and K277R for type II TβR. Inactivating or attenuating mutations in the genes for Type I and Type II TβR genes are found in a variety of cancers. In addition, signaling of TβRs is regulated by phosphorylation and dephosphorylation mechanisms, ubiquitinylation and sumoylation, and by endocytosis and by TACE-mediated ectodomain shedding of type I, but not type II receptors TACE, aka ADAM-17, which mediates shedding of cytokines, GF receptors, and adhesion proteins and is highly expressed in cancers.

The X-ray co-crystal structure of TβR I and FKBP12 has been described, and the kinase activation process was discussed. Meanwhile, several crystal structures can be found in the PDB data base: 1B6C, 1IAS, 1PY5, 1RW8, 1VJY, 2PJY, and a model 1TBI. For TβR II only X-ray studies for the extracellular ligand binding domain are known to the public: 1KTZ, 1M9Z, and 1PLO (NMR), but none of the kinase domain.

TGFβ signal transduction involves Smads, the only substrates for TβR type I receptor kinases. The human genome encodes eight Smads from 3 subfamilies (R-, Co-, I-Smads), which are ubiquitously expressed throughout development and in adult tissue. Smads not only are phosphorylated by Type I TGFβ receptor kinases but they are also regulated by oligomerisation, ubiquitinylation and degradation, and nucleoplasmatic shuttling.

It was shown that VEGF release is regulated by ALK1 and ALK5, whereas TGFβ enhanced and BMP-9 suppressed expression of VEGF.

Studies with truncated ALK4 isoforms suggest involvement of this type I kinase in growth and development of pituitary tumors, by a dominant negative inhibition of activin signaling. Studies of the spatiotemporal window of roles of ALK4 in embryonic development, regulation of the mesoderm induction, primitive streak formation, gastrulation, primary axis formation and left-right axis determination are still not clarifying the role of ALK4 in adult.

In a large scale human candidate screen it was found that dominant-negative ALK2 alleles are associated with congenital heart disease, like improper atrioventrikular septum development.

ALK1 binds TβR-II and Endoglin/CD105/TβR-III and phosphorylates SMAD-1 and -5. The role of endoglin and especially the differential modulation of TGFβ signaling by two variants, L- and S-endoglin, have been shown. ALK1 functions in vascular remodeling and is found with ALK5 in balancing the activation state of endothelium in inflamed tissue, wounds and tumor. ALK1 is expressed in lung, placenta, and other highly vascularized tissue, and is selectively found on ECs. In addition, ALK1 was detected on neurons.

Loss of expression of type II TβR correlates with high tumor grade in human breast carcinomas, indicating a contribution to breast cancer progression. Tumor growth can be characterized by deregulated i.e. autonomous cell growth due to perturbation of RTK signaling by mutations or other genetic alterations. Of the 32000 human coding genes which are involved in signal transduction, more than 520 protein kinases and 130 protein phosphatases exert tight and reversible control on protein phosphorylation. Selectivity is found for tyrosine and for serine/threonine phosphorylation. There are more than 90 known PTK genes in the human genome, more than 50 encode transmembrane RPTKs distributed in 20 subfamilies, and 32 encode cytoplasmic, non-receptor PTKs in 10 subfamilies. For example Trk A has an important role in thyroid carcinomas and neuroblastomas, EphB2 and B4 are over-expressed in carcinomas, Axl and Lck are over-expressed in leukemia.

TGFβ inhibitors for the treatment of cancer were reviewed. There are further indications and pathologies, indirect targeting cancer, wound healing and inflammation via anti-angiogenesis, blood vessel formation, stabilization, maintenance and regression.

Angiogenesis, the development of new vessels from pre-existing vessels, is critical in vascular development in embryogenesis, organogenesis, and wound healing. In addition to those physiological processes, angiogenesis is important for tumor growth, metastasis and inflammation, resulting in diseases like tumors of the breast, uterine cervix, uterine corpus (endometrium), ovary, lung, bronchus, liver, kidney, skin, oral cavity and pharynx, prostate, pancreas, urinary bladder, blood cells, colon, rectum, bone, brain, central and peripheral nervous system, exemplified as breast cancer, colorectal cancer, gliomas, lymphomas, and so on, and of inflammatory diseases like rheumatoid arthritis and psoriasis, or diseases of the eye, like macula degeneration, and diabetic retinopathy. Molecular mechanisms of blood vessel formation and the angiogenic switch in tumorigenesis were recently discussed. Vascular patterning is regulated by Eph receptor tyrosine kinases and ephrin ligands, e.g. ephrin-B2 signaling via Eph B4 and Eph B1. EphB4 controls vascular morphogenesis during postnatal angiogenesis. The maturation of nascent vasculature, formed by angiogenesis or vasculogenesis, requires mural cells (pericytes, smooth muscle cells), generation of extracellular matrix and specialization of the vessel wall for structural support and regulation of vessel function. Regulation of those processes and interaction between endothelial cells and their mural cells involves several ligand kinase pairs, like VEGF/VEGFR1, VEGFR2, EphrinB2/EphB4, PDGFR/PDGFRβ, Angiopoietins/TIE2, TGFβ/TGFβR-ALK1/ALK5. Vessel assembly, capillary formation, sprouting, stabilization and destabilization, even regression, is regulated by a functional balance of those kinases and ligands. Lymphangiogenesis is regulated via VEGF receptor 3 and its ligands VEGF C, and D, as well as TIE2 and its ligands angiopoietins 1, 2. Inhibition of VEGFR3 and/or TIE2 signaling and therefore inhibition of formation of lymphatic vessels can be a mean to stop metastasis of tumor cells. The whole body of information about pathological vascularisation leads to the assumption for inhibition of angiogenesis being a promising strategy for treatment of cancer and other disorders.

The importance of TGFβ receptors for angiogenic processes is shown by Alk1, endoglin, Alk5 and TβRII KO mice all exhibiting an embryonic lethal phenotype due to vascular defects. In addition, in ECs TGFβ ligands are able to stimulate two pathways, with Smad 1/5/8 phosphorylation downstream of Alk1 and Smad2/3 phosphorylation downstream of Alk5. Both pathways cross-talk with each other. Alk5 knock-in mice with L45 loop mutations show defective Smad activation. TGFβ/Alk5 signaling is antagonized by ALK1 in ECs.

TGFβ exists in at least five isoforms (TGFβ1-5), which are not related to TGFa, with TGFβ1 as the prevalent form. TGFβ is a ubiquitous and essential regulator of cellular and physiological processes including proliferation, differentiation, migration, cell survival, angiogenesis and immunosurveillance.

Since cancer cells express tumor-specific antigens they normally would be recognized by the immune system and would be destroyed. During tumorigenesis cancer cells acquire the ability to evade this immunosurveillance by multiple mechanisms. A major mechanism is cancer cell mediated immunosuppression by secretion of TGFβ, a potent immunosuppressive cytokine. TGFβ has the potential to switch from being a tumor suppressor to a tumor promoter and prometastatic factor. TGFβ function is transmitted by a tetrameric receptor complex, consisting of two groups of transmembrane serine-threonine kinase receptors, called type I and type II receptors, which are activated following engagement of members of the TGFβ superfamily of ligands, which is divided in 2 groups, the TGFβ/Activin and BMP/GDF branches. TGFβ1, 2, and 3 belong to the TGFβ/Activin branch of ligands. These binding events specify downstream responses that are differentially regulated in different cell types.

Importance of fibroblasts in mesenchymal-epithelial interaction in skin during wound repair was described in an inducible postnatal deletion of TGFβ RII in skin fibroblasts. During wound repair, expression of the ligand TGFβ and its receptor types RI and RII are timely and spatially regulated. CD109, a GPI linked cell surface antigen, expressed by CD34+ acute myeloid leukemia cell lines, ECs, activated platelets and T-cells are part of the TβR system in human keratinocytes. Follicle Stem Cells (FSCs) in the bulge region of hair follicle can give rise to multiple lineages during hair cycle and wound healing. Smad4, a common mediator of TGFβ signaling is part of FSCs maintenance. Smad4 KO studies in mouse skin showed hair follicle defects and squamous cell carcinoma formation. The potential suppression of TGFβ delayed catagen progression in hair follicles. The well described role of TGFβ in keratinocyte apoptosis during catagen phase is likely to involve anagen-specific hair follicle components also involving co-localized TβRI and TβRII.

Abnormal activity of TGFβ in fibrosis of several organs, such as skin, kidney, heart and liver, is known, being a rational for use of TβR inhibitors in fibrotic diseases. Systemic sclerosis (scleroderma), a complex disorder of connective tissue leading to fibrosis of the skin and inner organs, was shown to be TGFβ/receptor RI dependent. Pulmonary arterial hypertension (PAH) is a condition potentially treatable with ALK5 inhibitors because abnormal proliferation of peripheral arterial smooth muscle cells is driven by activated TGFβ receptors. Treatment in rats was successful with SB525334. Benefit in rat was also shown with IN-1233. Renal fibrosis can lead to diabetes.

Beneficial side effects of TβR kinase inhibitor derivatives and a connection between TGFβ signaling and hepatitis C virus (HCV) replication is known. TGFβ signaling is discussed as an emerging stem cell target in metastatic breast cancer. TGFβ1, 2, 3 and their receptors are expressed in neurons, astrocytes and microglia. Improvement of pathological outcome with TGFβ signaling modulators can be expected. The TGFβ superfamily in cardiovascular disease, like atherosclerosis, myocardial ischemia and cardiac remodeling is focus of an issue of cardiovascular research.

Further details on the biochemistry of TGFβ are disclosed in WO 2009/004753, which is incorporated in its entirety by reference in the disclosure of the invention hereby.

In addition, RON kinase is a valuable target in tumor biology (Wagh et al. (2008) Adv Cancer Res. 100:1-33). The Met-related receptor tyrosine kinase RON is involved in tumor growth and metastasis. The RON receptor is a member of the Met family of cell surface receptor tyrosine kinases and is primarily expressed on epithelial cells and macrophages. The biological response of RON is mediated by binding of its ligand, hepatocyte growth factor-like protein/macrophage stimulating-protein (HGFL). HGFL is primarily synthesized and secreted from hepatocytes as an inactive precursor and is activated at the cell surface. Binding of HGFL to RON activates RON and leads to the induction of a variety of intracellular signaling cascades that leads to cellular growth, motility and invasion. Recent studies have documented RON overexpression in a variety of human cancers including breast, colon, liver, pancreas, and bladder. Moreover, clinical studies have also shown that RON overexpression is associated with both worse patient outcomes as well as metastasis. Forced overexpression of RON in transgenic mice leads to tumorigenesis in both the lung and the mammary gland and is associated with metastatic dissemination. While RON overexpression appears to be a hallmark of many human cancers, the mechanisms by which RON induces tumorigenesis and metastasis are still unclear. Several strategies are currently being undertaken to inhibit RON as a potential therapeutic target; current strategies include the use of RON blocking proteins, small interfering RNA (siRNA), monoclonal antibodies, and small molecule inhibitors. In total, these data suggest that RON is a critical factor in tumorigenesis and that inhibition of this protein, alone or in combination with current therapies, may prove beneficial in the treatment of cancer patients.

In addition, TAK1, or CHK2 are valuable targets in immunity and cellular damage response pathways (Delaney & Mlodzik (2006) Cell Cycle 5(24): 2852-5, describing TGF-beta activated kinase-1 and new insights into the diverse roles of TAK1 in development and immunity. A number of recent publications have examined the role of TAK1 in model systems ranging from fly to mouse. Rather than fit into a clearly defined linear molecular pathway, TAK1 seems to act in a signaling nexus that responds to a variety of upstream signals, including inflammatory molecules and developmental cues. TAK1 then influences a number of downstream processes ranging from innate immune responses to patterning and differentiation via JNK, NFkappaB and TCFbeta-catenin signaling. These differences in function are not simply a matter of cell type. For example, NFkappaB signaling in a particular cell may or may not require TAK1 depending on the nature of the activating signal. Interestingly, the multi-task functionality of TAK1 is conserved between vertebrate and invertebrate species. Studies of TAK1 in multiple experimental systems are likely to reveal more roles for this kinase and also elucidate mechanisms by which other signaling molecules fulfill diverse signaling roles.

Furthermore, the checkpoint kinases, Chk1 and Chk2 are Ser/Thr protein kinases, which function as key regulatory kinases in cellular DNA damage response pathways limiting cell-cycle progression in the presence of DNA damage. The development of checkpoint kinase inhibitors for the treatment of cancer has been a major objective in drug discovery over the past decade, as evidenced by three checkpoint kinase inhibitors entering clinic trials since late 2005. A large number of chemically diverse Chk1 and Chk2 kinase inhibitors have appeared in the recent patent literature. Common structural motifs of the checkpoint kinase inhibitors were identified. There are currently three checkpoint kinase inhibitors in clinical development, a continuing effort by the pharmaceutical industry to identify novel scaffolds for checkpoint kinase inhibition (Janetka & Ashwell (2009) Expert Opin Ther Pat. 2009 19(2): 165-97).

Further prior art documents are as follows:

WO 99/42463 discloses substituted quinoxaline derivatives as interleukin-8-receptor antagonists. The international application does not disclose pyrido[2,3-b]pyrazine derivatives nor does it describe the inhibition, regulation and/or modulation of signal transduction by ATP consuming proteins such as TGF-beta receptor kinases.

WO 00/12497 describes quinazoline derivatives as medicaments. The international application does not disclose pyrido[2,3-b]pyrazine derivatives.

WO 03/097615 relates to the treatment of fibroproliferative disorders using TGF-β inhibitors. The international application does not disclose pyrido[2,3-b]pyrazine derivatives.

WO 2004/010929 is directed to methods for improvement of lung function using TGF-β inhibitors. The international application does not disclose pyrido[2,3-b]pyrazine derivatives.

WO 2005/007652 discloses substituted quinolin-4-ylamine analogues. The international application among others discloses pyrido[2,3-b]pyrazine derivatives. However, these show a different substitution pattern as compared to the pyrido[2,3-b]pyrazine derivatives of the present invention. The international application does not describe the inhibition, regulation and/or modulation of signal transduction by ATP consuming proteins such as TGF-beta receptor kinases.

WO 2005/023807 describes substituted bicyclic quinazolin-4-ylamine derivatives. The international application does not disclose pyrido[2,3-b]pyrazine derivatives nor does it describe the inhibition, regulation and/or modulation of signal transduction by ATP consuming proteins such as TGF-beta receptor kinases.

WO 2005/042498 relates to capsaicin receptor agonists. The international application does not disclose pyrido[2,3-b]pyrazine derivatives nor does it describe the inhibition, regulation and/or modulation of signal transduction by ATP consuming proteins such as TGF-beta receptor kinases.

WO 2005/065691 is directed to the treatment of malignant gliomas with TGF-β inhibitors. The international application does not disclose pyrido[2,3-b]pyrazine derivatives.

WO 2006/042289 deals with substituted biaryl quinolin-4-ylamine analogues. The international application among others discloses pyrido[2,3-b]pyrazine derivatives. However, these show a different substitution pattern as compared to the pyrido[2,3-b]pyrazine derivatives of the present invention. The international application does not describe the inhibition, regulation and/or modulation of signal transduction by ATP consuming proteins such as TGF-beta receptor kinases.

WO 2006/076646 discloses heteroaryl substituted quinolin-4-ylamine analogues. The international application among others discloses pyrido[2,3-b]pyrazine derivatives. However, these show a different substitution pattern as compared to the pyrido[2,3-b]pyrazine derivatives of the present invention. The international application does not describe the inhibition, regulation and/or modulation of signal transduction by ATP consuming proteins such as TGF-beta receptor kinases.

WO 2008/138878 describes novel pyridopyrazine derivatives, process of manufacturing and uses thereof. However, these show a different substitution pattern as compared to the pyrido[2,3-b]pyrazine derivatives of the present invention. The international application does not describe the inhibition, regulation and/or modulation of signal transduction by ATP consuming proteins such as TGF-beta receptor kinases.

The citation of any reference in this application is not an admission that the reference is relevant prior art to this application.

DESCRIPTION OF THE INVENTION

The present invention has the object to provide novel pyrido[2,3-b]pyrazine derivatives.

The object of the present invention has surprisingly been solved in one aspect by providing compounds of formula (I)

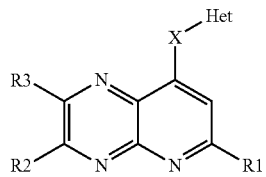

(I)

wherein:
X denotes absent, NR4 or CR5R6;
R1 denotes monocyclic aryl having 3, 4, 5, 6, 7 or 8 C atoms or a monocyclic heteroaryl having 1, 2, 3, 4, 5, 6, 7 or 8 C atoms and 1, 2, 3, 4 or 5 N, O and/or S atoms, each of which can independently from each other be substituted by at least one substituent selected from the group consisting of Y, Hal, CN, $CF_3$, OY;

R2 denotes H, A, —OY, —$NH_2$ or —NAA;

R3 denotes H, A, —OY or —NYY;

R4, R5, R6 independently from each other denote absent, H, A;

R7 denotes Hal, A, —$(CYY)_n$—OY, —$(CYY)_n$—NYY, $(CYY)_n$-Het$^2$, $(CYY)_n$—O-Het$^2$, SY, $NO_2$, CN, COOY, —CO—NYY, —NY—COA, —NY—$SO_2$A, —$SO_2$—NYY, $S(O)_m$A, —CO-Het$^2$, —O$(CYY)_n$—NYY, —O$(CYY)_n$-Het$^2$, —NH—COOA, —NH—CO—NYY, —NH—COO—$(CYY)_n$—NYY, —NH—COO—$(CYY)_n$-Het$^2$, —NH—CO—NH—$(CYY)_n$—NYY, —NH—CO—NH$(CYY)_n$-Het$^2$, —OCO—NH—$(CYY)_n$—NYY, —OCO—NH—$(CYY)_n$-Het$^2$, CHO, COA, =S, =NY, =O;

Y denotes H or A;

A denotes unbranched or branched alkyl having 1, 2, 3, 4, 5, 6, 7, 8, 9 or 10 C atoms, in which 1, 2, 3, 4, 5, 6 or 7 H atoms can be replaced independently from one another by Hal and/or in which one or two $CH_2$ groups can be replaced independently of one another by a O, S, SO, $SO_2$, a —CY=CY— group and/or a —C≡C— group, or denotes cyclic alkyl with 3, 4, 5, 6 or 7 C atoms;

Het denotes a saturated or unsaturated, mono-, bi- or tricyclic heterocycle having 3, 4, 5, 6, 7, 8, 9, 10, 11, 12, 13, 14, 15, 16, 17, 18, 19 or 20 C atoms and 1, 2, 3, 4 or 5 N, O and/or S atoms, which can independently from each other be substituted by at least one substituent R7;

Het$^2$ denotes a saturated or unsaturated, mono-, bi- or tricyclic heterocycle having 3, 4, 5, 6, 7, 8, 9, 10, 11, 12, 13, 14, 15, 16, 17, 18, 19 or 20 C atoms and 1, 2, 3, 4 or 5 N, O and/or S atoms, which can independently from each other be substituted by at least one substituent selected from the group of Hal, A, —$(CYY)_n$—OY, —$(CYY)_n$—NYY, $(CYY)_n$-Het$^3$, $(CYY)_n$—O-Het$^3$, SY, $NO_2$, CN, COOY, —CO—NYY, —NY—COA, —NY—$SO_2$A, —$SO_2$—NYY, $S(O)_m$A, —CO-Het$^3$, —O$(CYY)_n$—NYY, —O$(CYY)_n$-Het$^3$, —NH—COOA, —NH—CO—NYY, —NH—COO—$(CYY)_n$—NYY, —NH—COO—$(CYY)_n$—Het$^3$, —NH—CO—NH—$(CYY)_n$—NYY, —NH—CO—NH$(CYY)_n$—Het$^3$, —OCO—NH—$(CYY)_n$—NYY, —OCO—NH—$(CYY)_n$-Het$^3$, CHO, COA, =S, =NY, =O;

Het$^3$ denotes a saturated or unsaturated, mono-, bi- or tricyclic heterocycle having 3, 4, 5, 6, 7, 8, 9, 10, 11, 12, 13, 14, 15, 16, 17, 18, 19 or 20 C atoms and 1, 2, 3, 4 or 5 N, O and/or S atoms, which can independently from each other be substituted by at least one substituent selected from the group of Hal, A, —$(CYY)_n$—OY, —$(CYY)_n$—NYY, SY, $NO_2$, CN, COOY, —CO—NYY, —NY—COA, —NY—$SO_2$A, —$SO_2$—NYY, $S(O)_m$A, —NH—COOA, —NH—CO—NYY, CHO, COA, =S, =NY, =O;

Hal denotes F, Cl, Br or I;

m denotes 0, 1, or 2;

n denotes 0, 1, 2, 3 or 4;

and the physiologically acceptable salts, solvates, tautomers and stereoisomers thereof, including mixtures thereof in all ratios.

In a preferred embodiment, a compound according to formula (II) is provided,

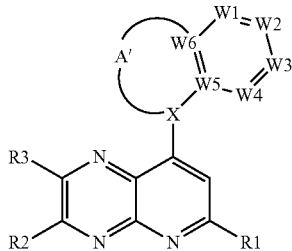

(II)

wherein:
A' denotes absent or together with X and W5 and W6 denotes mono- or bicyclic aryl having 3, 4, 5, 6, 7, 8, 9 or 10 C atoms, each of which can independently from each other be substituted by at least one substituent R7 as defined supra, or together with X and W5 and W6 denotes Het as defined supra;
X denotes absent, NR4 or CR5R6 with R4, R5, R6 being as defined supra or together with A' and W5 and W6 denotes mono- or bicyclic aryl having 3, 4, 5, 6, 7, 8, 9 or 10 C atoms, each of which can independently from each other be substituted by at least one substituent R7 as defined supra, or together with A' and W5 and W6 denotes Het as defined supra; with the first proviso that if X is absent A' is also absent and W5 is directly linked to the pyrido[2,3-b]pyrazine moiety, and with the second proviso that if X is NR4 W5 is CR8;
W1, W2, W3, independently from each other denote N or CR8, with the
W4, W5, W6 proviso that at least one of W1, W2, W3, W4, W5, W6 is N;
R8 denotes absent, H, A, —OY, —NYY, —NY—COY or Het², with Y and Het² being as defined supra, where in case Het² refers to Het³, Het³ being also as defined supra;
and the physiologically acceptable salts, solvates, tautomers and stereoisomers thereof, including mixtures thereof in all ratios.

In a preferred embodiment, a compound according to formula (I) or formula (II) is provided, wherein:
X denotes NR4 or CR5R6 with R4, R5, R6 being as defined supra, preferably denotes NR4, and wherein in case of formula (II) A' is absent;
and the physiologically acceptable salts, solvates, tautomers and stereoisomers thereof, including mixtures thereof in all ratios.

In a preferred embodiment, a compound according to formula (I) and formula (II) is provided, wherein:
in case of formula (I) X is absent or wherein in case of formula (II) X and A' are both absent and W5 is directly linked to the pyrido[2,3-b]pyrazine moiety or wherein in case of formula (II) X together with A' and W5 and W6 denotes mono- or bicyclic aryl having 3, 4, 5, 6, 7, 8, 9 or 10 C atoms, each of which can independently from each other be substituted by at least one substituent R7 as defined supra, or wherein in case of formula (II) X together with A' and W5 and W6 denotes Het as defined supra;
and the physiologically acceptable salts, solvates, tautomers and stereoisomers thereof, including mixtures thereof in all ratios.

In a preferred embodiment, a compound according to formula (I) and formula (II) and above embodiments is provided, wherein:
in case of formula (I) Het and in case of formula (II) X together with A' and W5 and W6 and the heterocycle consisting of W1 to W6 are independently from each other selected from the group consisting of: pyridinyl, pyridin-3-yl, pyridin-4-yl, naphthyridinyl, [2,7]naphthyridin-1-yl, [3,7]naphthyridin-1-yl, [2,6]naphthyridin-1-yl, isoquinolinyl, isoquinolin-1-yl, pyrrolopyridinyl, pyrrolo[3,2-c]pyridin-1-yl, furopyridinyl, furo[3,2-b]pyridin-7-yl;
and the physiologically acceptable salts, solvates, tautomers and stereoisomers thereof, including mixtures thereof in all ratios.

In a preferred embodiment, a compound according to formula (I) and formula (II) and above embodiments is provided, wherein:
R2 and R3 denote H;
and the physiologically acceptable salts, solvates, tautomers and stereoisomers thereof, including mixtures thereof in all ratios.

In a preferred embodiment, a compound according to formula (II) and above embodiments is provided, wherein:
W1, W2, W3, one of W1, W2 or W3 is N and the other W are CR8, with
W4, W5, W6 R8 being defined as supra;
and the physiologically acceptable salts, solvates, tautomers and stereoisomers thereof, including mixtures thereof in all ratios.

In a preferred embodiment, a compound according to formula (I) and formula (II) and above embodiments is provided, wherein:
R4 denotes H;
and the physiologically acceptable salts, solvates, tautomers and stereoisomers thereof, including mixtures thereof in all ratios.

In a preferred embodiment, a compound according to formula (I) and formula (II) and above embodiments is provided, wherein:
R1 denotes monocyclic aryl having 5 or 6 C atoms which can be substituted by at least one substituent selected from the group consisting of Y, Hal, CN, CF₃, OY, with Y, Hal being defined as supra;
and the physiologically acceptable salts, solvates, tautomers and stereoisomers thereof, including mixtures thereof in all ratios.

In a preferred embodiment, a compound according to formula (I) and formula (II) and above embodiments is provided, wherein:
R7 denotes A, —(CYY)$_n$—NYY, —(CYY)$_n$-Het², with Y, n, Het² being defined as supra;
and the physiologically acceptable salts, solvates, tautomers and stereoisomers thereof, including mixtures thereof in all ratios.

In a preferred embodiment, a compound according to formula (I) and formula (II) and above embodiments is provided, wherein:
R8 denotes absent, H, A, —NYY or Het², with Y, Het² being defined as supra;
and the physiologically acceptable salts, solvates, tautomers and stereoisomers thereof, including mixtures thereof in all ratios.

In a preferred embodiment, a compound according to formula (I) and formula (II) and above embodiments is provided, wherein:

Y denotes H or A;

and the physiologically acceptable salts, solvates, tautomers and stereoisomers thereof, including mixtures thereof in all ratios.

In a preferred embodiment, a compound according to formula (I) and formula (II) and above embodiments is provided, wherein:

A denotes unbranched or branched alkyl having 1, 2, 3, 4, 5, 6, 7 or 8 C atoms;

and the physiologically acceptable salts, solvates, tautomers and stereoisomers thereof, including mixtures thereof in all ratios.

In a preferred embodiment, a compound according to formula (I) and formula (II) and above embodiments is provided, wherein:

Hal denotes F or Cl;

and the physiologically acceptable salts, solvates, tautomers and stereoisomers thereof, including mixtures thereof in all ratios.

In a preferred embodiment, a compound according to formula (I) and formula (II) and above embodiments is provided, wherein:

n is 0, 1 or 2;

and the physiologically acceptable salts, solvates, tautomers and stereoisomers thereof, including mixtures thereof in all ratios.

In a preferred embodiment, a compound according to formula (I) and formula (II) and above embodiments is provided, wherein:

X in case of formula (I) or formula (II) is absent or denotes NR4, wherein in case of formula (II) if X is absent, A' is also absent and W5 is directly linked to the pyrido[2,3-b]pyrazine moiety; or X, A', W5, W6 in case of formula (II) together denote monocyclic aryl having 5 or 6 C atoms, each of which can independently from each other be substituted by at least one substituent R7, or together denote Het; and Het denotes a saturated or unsaturated, mono- or bicyclic heterocycle having 3, 4, 5, 6, 7, 8 or 9 C atoms and 1 or 2 N atoms, which can independently from each other be substituted by at least one substituent R7; and $Het^2$ denotes a saturated or unsaturated, mono- or bicyclic heterocycle having 3, 4, 5, 6, 7, 8 or 9 C atoms and 1 or 2 N atoms, which can independently from each other be substituted by at least one substituent selected from the group of Hal, A, —(CYY)$_n$—OY or —(CYY)$_n$-Het$^3$; and $Het^3$ denotes a saturated or unsaturated, mono- or bicyclic heterocycle having 3, 4, 5, 6, 7, 8 or 9 C atoms and 1 or 2 N atoms, which can independently from each other be substituted by at least one substituent selected from the group of Hal or A; and W1, W2, W3, in case of formula (II) independently from each other W4, W5, W6 denote N or CR8, with the proviso that at least one of W1, W2, W3, W4, W5, W6 is N; preferably one of W1, W2 or W3 is N and the other W are CR8; and R1 denotes monocyclic aryl having 5 or 6 C atoms which can be substituted by at least one substituent selected from the group consisting of Y, Hal, CN, CF$_3$, OY; and R2, R3, R4 independently from each other denote H or A; and R7 denotes A, —(CYY)$_n$—NYY, —(CYY)$_n$-Het$^2$; and R8 denotes absent, H, A, —NYY or Het$^2$; and Y denotes H or A; and A denotes unbranched or branched alkyl having 1, 2, 3, 4, 5, 6, 7 or 8 C atoms; and Hal denotes F or Cl; and n is 0, 1 or 2;

and the physiologically acceptable salts, solvates, tautomers and stereoisomers thereof, including mixtures thereof in all ratios.

In another aspect, the object of the present invention has surprisingly been solved by providing a compound selected from the group consisting of:

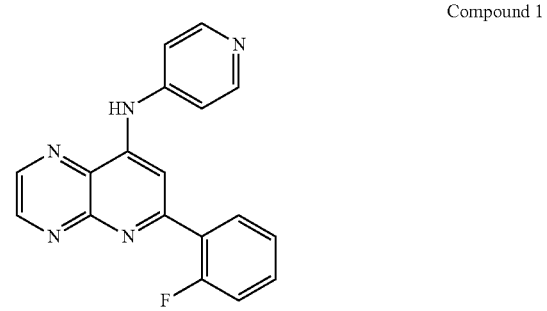

Compound 1

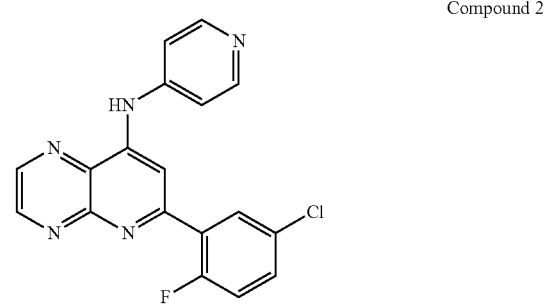

Compound 2

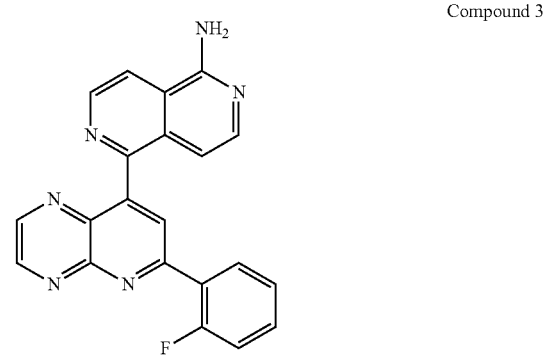

Compound 3

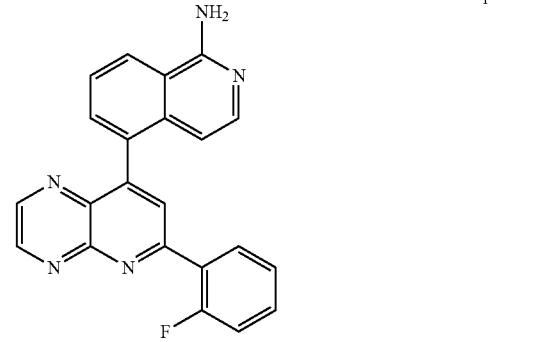

Compound 4

-continued
Compound 5
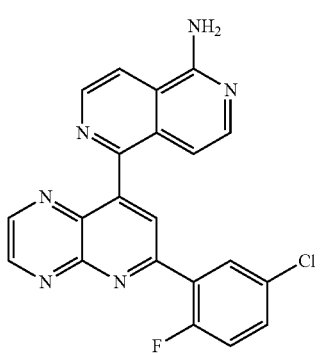
Compound 6
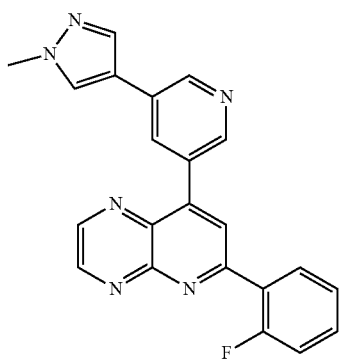
Compound 7
Compound 8
-continued
Compound 9
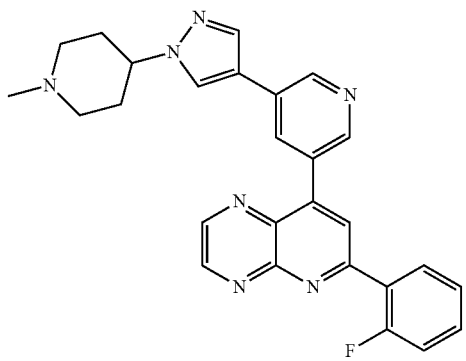
Compound 10
Compound 11
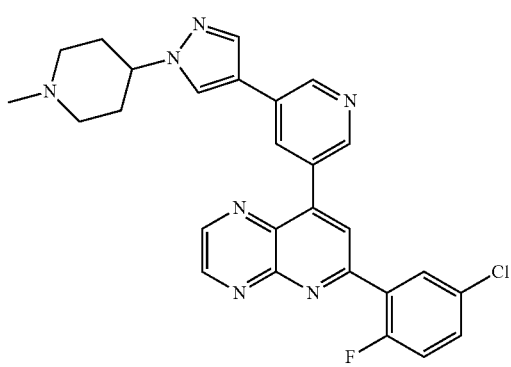
Compound 12
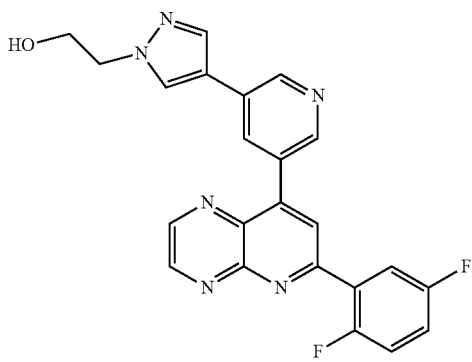

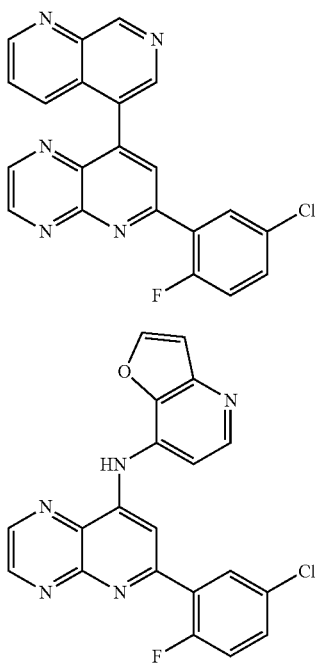

Compound 13

Compound 14 and the physiologically acceptable salts, solvates, tautomers and stereoisomers thereof, including mixtures thereof in all ratios.

For the avoidance of doubt, if chemical name and chemical structure of the above illustrated compounds do not correspond by mistake, the chemical structure is regarded to unambiguously define the compound.

All the above generically or explicitly disclosed compounds, including preferred subsets/embodiments of the herein disclosed formula (I) and formula (II) and Compounds 1 to 14, are hereinafter referred to as compounds of the (present) invention.

The nomenclature as used herein for defining compounds, especially the compounds according to the invention, is in general based on the rules of the IUPAC organisation for chemical compounds and especially organic compounds.

The terms indicated for explanation of the above compounds of the invention always, unless indicated otherwise in the description or in the claims, have the following meanings:

The term "unsubstituted" means that the corresponding radical, group or moiety has no substituents.

The term "substituted" means that the corresponding radical, group or moiety has one or more substituents. Where a radical has a plurality of substituents, and a selection of various substituents is specified, the substituents are selected independently of one another and do not need to be identical.

The terms "alkyl" or "A" as well as other groups having the prefix "alk" for the purposes of this invention refer to acyclic saturated or unsaturated hydrocarbon radicals which may be branched or straight-chain and preferably have 1 to 10 carbon atoms, i.e. $C_1$-$C_{10}$-alkanyls, $C_2$-$C_{10}$-alkenyls and $C_2$-$C_{10}$-alkynyls. Alkenyls have at least one C—C double bond and alkynyls at least one C—C triple bond. Alkynyls may additionally also have at least one C—C double bond. Examples of suitable alkyl radicals are methyl, ethyl, n-propyl, isopropyl, n-butyl, isobutyl, sec-butyl, tert-butyl, n-pentyl, iso-pentyl, neo-pentyl, tert-pentyl, 2- or 3-methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosanyl, ethylenyl (vinyl), propenyl (—CH$_2$CH=CH$_2$; —CH=CH—CH$_3$, —C(=CH$_2$)—CH$_3$), butenyl, pentenyl, hexenyl, heptenyl, octenyl, octadienyl, octadecenyl, octadec-9-enyl, icosenyl, icos-11-enyl, (Z)-icos-11-enyl, docosnyl, docos-13-enyl, (Z)-docos-13-enyl, ethynyl, propynyl (—CH$_2$—C≡CH, —C≡CH$_3$), butynyl, pentynyl, hexynyl, heptynyl, octynyl. Especially preferred is $C_{1-4}$-alkyl. A $C_{1-4}$-alkyl radical is for example a methyl, ethyl, propyl, isopropyl, butyl, isobutyl, tert-butyl.

The term "cycloalkyl" for the purposes of this invention refers to saturated and partially unsaturated non-aromatic cyclic hydrocarbon groups/radicals, having 1 to 3 rings, that contain 3 to 20, preferably 3 to 12, most preferably 3 to 8 carbon atoms. The cycloalkyl radical may also be part of a bi- or polycyclic system, where, for example, the cycloalkyl radical is fused to an aryl, heteroaryl or heterocyclyl radical as defined herein by any possible and desired ring member(s). The bonding to the compounds of the general formula can be effected via any possible ring member of the cycloalkyl radical. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl. Especially preferred are $C_3$-$C_9$-cycloalkyl and $C_4$-$C_8$-cycloalkyl. A $C_4$-$C_8$-cycloalkyl radical is for example a cyclobutyl, cyclopentyl, cyclohexyl, cycloheptyl, cyclooctyl.

The term "heterocyclyl" or "heterocycle" for the purposes of this invention refers to a mono- or polycyclic system of 3 to 20, preferably 5 or 6 to 14 ring atoms comprising carbon atoms and 1, 2, 3, 4, or 5 heteroatoms, in particular nitrogen, oxygen and/or sulfur which are identical or different. The cyclic system may be saturated, mono- or polyunsaturated but may not be aromatic. In the case of a cyclic system consisting of at least two rings the rings may be fused or spiro- or otherwise connected. Such "heterocyclyl" radicals can be linked via any ring member. The term "heterocyclyl" also includes systems in which the heterocycle is part of a bi- or polycyclic saturated, partially unsaturated and/or aromatic system, such as where the heterocycle is fused to an "aryl", "cycloalkyl", "heteroaryl" or "heterocyclyl" group as defined herein via any desired and possible ring member of the heterocycyl radical. The bonding to the compounds of the general formula can be effected via any possible ring member of the heterocycyl radical. Examples of suitable "heterocyclyl" radicals are pyrrolidinyl, thiapyrrolidinyl, piperidinyl, piperazinyl, oxapiperazinyl, oxapiperidinyl, oxadiazolyl, tetrahydrofuryl, imidazolidinyl, thiazolidinyl, tetrahydropyranyl, morpholinyl, tetrahydrothiophenyl, dihydropyranyl, indolinyl, indolinylmethyl, imidazolidinyl, 2-aza-bicyclo[2.2.2] octanyl.

The term "aryl" for the purposes of this invention refers to a mono- or polycyclic aromatic hydrocarbon systems having 3 to 14, preferably 5 to 14, more preferably 5 to 10 carbon atoms. The term "aryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the aryl radical. The bonding to the compounds of the general formula can be effected via any possible ring member of the aryl radical. Examples of suitable "aryl" radicals are phenyl, biphenyl, naphthyl, 1-naphthyl, 2-naphthyl and anthracenyl, but likewise indanyl, indenyl, or 1,2,3,4-tetrahydronaphthyl. The most preferred aryl is phenyl.

The term "heteroaryl" for the purposes of this invention refers to a 3 to 15, preferably 5 to 14, more preferably 5-, 6- or 7-membered mono- or polycyclic aromatic hydrocarbon radical which comprises at least 1, where appropriate also 2, 3, 4 or 5 heteroatoms, preferably nitrogen, oxygen and/or sulfur, where the heteroatoms are identical or different. The number of nitrogen atoms is preferably 0, 1, 2, or 3, and that of the oxygen and sulfur atoms is independently 0 or 1. The term "heteroaryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the heteroaryl radical. The bonding to the compounds of the general formula can be effected via any possible ring member of the heteroaryl radical. Examples of suitable "heteroaryl" are acridinyl, benzdioxinyl, benzimidazolyl, benzisoxazolyl, benzodioxolyl, benzofuranyl, benzothiadiazolyl, benzothiazolyl, benzothienyl, benzoxazolyl, carbazolyl, cinnolinyl, dibenzofuranyl, dihydrobenzothienyl, furanyl, furazanyl, furyl, imidazolyl, indazolyl, indolinyl, indolizinyl, indolyl, isobenzylfuranyl, isoindolyl, isoquinolinyl, isoquinolyl, isothiazolyl, isoxazolyl, naphthyridinyl, oxadiazolyl, oxazolyl, phenazinyl, phenothiazinyl, phenoxazinyl, phthalazinyl, pteridinyl, purinyl, pyrazinyl, pyrazolyl, pyridazinyl, pyridinyl, pyridyl, pyrimidinyl, pyrimidyl, pyrrolyl, quinazolinyl, quinolinyl, quinolyl, quinoxalinyl, tetrazolyl, thiadiazolyl, thiazolyl, thienyl, thiophenyl, triazinyl, triazolyl.

For the purposes of the present invention, the terms "alkylcycloalkyl", "cycloalkylalkyl", "alkyl-heterocyclyl", "heterocyclylalkyl", "alkyl-aryl", "arylalkyl", "alkyl-heteroaryl" and "heteroarylalkyl" mean that alkyl, cycloalkyl, heterocycl, aryl and heteroaryl are each as defined above, and the cycloalkyl, heterocyclyl, aryl and heteroaryl radical is bonded to the compounds of the general formula via an alkyl radical, preferably $C_1$-$C_8$-alkyl radical, more preferably $C_1$-$C_4$-alkyl radical.

The term "alkyloxy" or "alkoxy" for the purposes of this invention refers to an alkyl radical according to above definition that is attached to an oxygen atom. The attachment to the compounds of the general formula is via the oxygen atom. Examples are methoxy, ethoxy and n-propyloxy, propoxy, isopropoxy. Preferred is "$C_1$-$C_4$-alkyloxy" having the indicated number of carbon atoms.

The term "cycloalkyloxy" or "cycloalkoxy" for the purposes of this invention refers to a cycloalkyl radical according to above definition that is attached to an oxygen atom. The attachment to the compounds of the general formula is via the oxygen atom. Examples are cyclopropyloxy, cyclobutyloxy, cyclopentyloxy, cyclohexyloxy, cycloheptyloxy, cyclooctyloxy. Preferred is "$C_3$-$C_9$cycloalkyloxy" having the indicated number of carbon atoms.

The term "heterocyclyloxy" for the purposes of this invention refers to a heterocyclyl radical according to above definition that is attached to an oxygen atom. The attachment to the compounds of the general formulae is via the oxygen atom. Examples are pyrrolidinyloxy, thiapyrrolidinyloxy, piperidinyloxy, piperazinyloxy.

The term "aryloxy" for the purposes of this invention refers to an aryl radical according to above definition that is attached to an oxygen atom. The attachment to the compounds of the general formula is via the oxygen atom. Examples are phenyloxy, 2-naphthyloxy, 1-naphthyloxy, biphenyloxy, indanyloxy. Preferred is phenyloxy.

The term "heteroaryloxy" for the purposes of this invention refers to a heteroaryl radical according to above definition that is attached to an oxygen atom. The attachment to the compounds of the general formula is via the oxygen atom. Examples are pyrrolyloxy, thienyloxy, furyloxy, imidazolyloxy, thiazolyloxy.

The term "carbonyl" or "carbonyl moiety" for the purposes of this invention refers to a —C(O)— group.

The term "alkylcarbonyl" for the purposes of this invention refers to a "alkyl-C(O)—" group, wherein alkyl is as defined herein.

The term "alkoxycarbonyl" or "alkyloxycarbonyl" for the purposes of this invention refers to a "alkyl-O—C(O)—" group, wherein alkyl is as defined herein.

The term "alkoxyalkyl" for the purposes of this invention refers to a "alkyl-O-alkyl-" group, wherein alkyl is as defined herein.

The term "haloalkyl" for the purposes of this invention refers to an alkyl group as defined herein comprising at least one carbon atom substituent with at least one halogen as defined herein.

The term "halogen", "halogen atom", "halogen substituent" or "Hal" for the purposes of this invention refers to one or, where appropriate, a plurality of fluorine (F, fluoro), bromine (Br, bromo), chlorine (Cl, chloro), or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. "Halogen" preferably means a fluorine, chlorine or bromine atom. Fluorine is most preferred, when the halogens are substituted on an alkyl (haloalkyl) or alkoxy group (e.g. $CF_3$ and $CF_3O$).

The term "hydroxyl" or "hydroxy" means an OH group.

The term "composition", as in pharmaceutical composition, for the purposes of this invention is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The terms "administration of" and "administering a" compound should be understood to mean providing a compound of the invention or a prodrug of a compound of the invention to the individualist need.

As used herein, the term "effective amount" refers to any amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

All stereoisomers of the compounds of the invention are contemplated, either in a mixture or in pure or substantially pure form. The compounds of the invention can have asymmetric centers at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers.

Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or nonchiral phases or by recrystallization from an optionally optically active solvent or with use of an optically active acid or base or by derivatization with an optically active reagent such as, for example, an optically active alcohol, and subsequent elimination of the radical.

The compounds of the invention may be present in the form of their double bond isomers as "pure" E or Z isomers, or in the form of mixtures of these double bond isomers.

Where possible, the compounds of the invention may be in the form of the tautomers, such as keto-enol tautomers.

It is likewise possible for the compounds of the invention to be in the form of any desired prodrugs such as, for example, esters, carbonates, carbamates, ureas, amides or phosphates, in which cases the actually biologically active form is released only through metabolism. Any compound that can be converted in vivo to provide the bioactive agent (i.e. compounds of the invention) is a prodrug within the scope and spirit of the invention.

Various forms of prodrugs are well known in the art and are described for instance in:
(i) Wermuth C G et al., Chapter 31: 671-696, The Practice of Medicinal Chemistry, Academic Press 1996;
(ii) Bundgaard H, Design of Prodrugs, Elsevier 1985; and
(iii) Bundgaard H, Chapter 5: 131-191, A Textbook of Drug Design and Development, Harwood Academic Publishers 1991.

Said references are incorporated herein by reference.

It is further known that chemical substances are converted in the body into metabolites which may where appropriate likewise elicit the desired biological effect—in some circumstances even in more pronounced form.

Any biologically active compound that was converted in vivo by metabolism from any of the compounds of the invention is a metabolite within the scope and spirit of the invention.

The compounds of the invention can, if they have a sufficiently basic group such as, for example, a secondary or tertiary amine, be converted with inorganic and organic acids into salts. The pharmaceutically acceptable salts of the compounds of the invention are preferably formed with hydrochloric acid, hydrobromic acid, iodic acid, sulfuric acid, phosphoric acid, methanesulfonic acid, p-toluenesulfonic acid, carbonic acid, formic acid, acetic acid, sulfoacetic acid, trifluoroacetic acid, oxalic acid, malonic acid, maleic acid, succinic acid, tartaric acid, racemic acid, malic acid, embonic acid, mandelic acid, fumaric acid, lactic acid, citric acid, taurocholic acid, glutaric acid, stearic acid, glutamic acid or aspartic acid. The salts which are formed are, inter alia, hydrochlorides, chlorides, hydrobromides, bromides, iodides, sulfates, phosphates, methanesulfonates, tosylates, carbonates, bicarbonates, formates, acetates, sulfoacetates, triflates, oxalates, malonates, maleates, succinates, tartrates, malates, embonates, mandelates, fumarates, lactates, citrates, glutarates, stearates, aspartates and glutamates. The stoichiometry of the salts formed from the compounds of the invention may moreover be an integral or non-integral multiple of one.

The compounds of the invention can, if they contain a sufficiently acidic group such as, for example, the carboxy, sulfonic acid, phosphoric acid or a phenolic group, be converted with inorganic and organic bases into their physiologically tolerated salts. Examples of suitable inorganic bases are ammonium, sodium hydroxide, potassium hydroxide, calcium hydroxide, and of organic bases are ethanolamine, diethanolamine, triethanolamine, ethylenediamine, t-butylamine, t-octylamine, dehydroabietylamine, cyclohexylamine, dibenzylethylene-diamine and lysine. The stoichiometry of the salts formed from the compounds of the invention can moreover be an integral or non-integral multiple of one.

It is likewise possible for the compounds of the invention to be in the form of their solvates and, in particular, hydrates which can be obtained for example by crystallization from a solvent or from aqueous solution. It is moreover possible for one, two, three or any number of solvate or water molecules to combine with the compounds of the invention to give solvates and hydrates.

By the term "solvate" is meant a hydrate, an alcoholate, or other solvate of crystallization.

It is known that chemical substances form solids which exist in different order states which are referred to as polymorphic forms or modifications. The various modifications of a polymorphic substance may differ greatly in their physical properties. The compounds of the invention can exist in various polymorphic forms and certain modifications may moreover be metastable. All these polymorphic forms of the compounds are to be regarded as belonging to the invention.

The compounds of the invention are surprisingly characterized by a strong and/or selective inhibition of ATP consuming proteins, preferably tyrosine kinases and serine/threonine kinases, more preferably TGF-beta, RON, TAK1, CHK2, PDK1, Met, PKD1, MINK1, SAPK2-alpha, SAPK2-beta, MKK1, GCK, HER4, ALK1, ALK2, ALK4, ALK5 and TbR type II. It is more preferred to inhibit serine/threonine kinases. Most preferred kinases to be inhibited are TGF-beta receptor kinase, RON, TAK1, PKD1, MINK1, SAPK2-alpha, SAPK2-beta and/or CHK2, highly preferably TGF-beta receptor kinase.

Due to their surprisingly strong and/or selective enzyme inhibition, the compounds of the invention can be advantageously administered at lower doses compared to other less potent or selective inhibitors of the prior art while still achieving equivalent or even superior desired biological effects. In addition, such a dose reduction may advantageously lead to less or even no medicinal adverse effects. Further, the high inhibition selectivity of the compounds of the invention may translate into a decrease of undesired side effects on its own regardless of the dose applied.

The compounds of the invention being ATP consuming protein inhibitors generally have an inhibition constant $IC_{50}$ of less than about 10 µM, and preferably less than about 1 µM.

The compounds according to the invention preferably exhibit an advantageous biological activity, which is easily demonstrated in enzyme-based assays, for example assays as described herein. In such enzyme-based assays, the compounds according to the invention preferably exhibit and cause an inhibiting effect, which is usually documented by $IC_{50}$ values in a suitable range, preferably in the micromolar range and more preferably in the nanomolar range.

As discussed herein, these signaling pathways are relevant for various diseases. Accordingly, the compounds according to the invention are useful in the prophylaxis and/or treatment of diseases that are dependent on the said signaling pathways by interaction with one or more of the said signaling pathways. The present invention therefore relates to compounds according to the invention as promoters or inhibitors, preferably as inhibitors, of the signaling pathways described herein, particularly the TGF-β signaling pathway.

The object of the present invention has surprisingly been solved in another aspect by providing the use of a compound of the invention for inhibiting ATP consuming proteins, preferably TGF-beta receptor kinase, RON, TAK1, PKD1, MINK1, SAPK2-alpha, SAPK2-beta and/or CHK2.

The terms "inhibiting, inhibition and/or retardation" are intended to refer for the purposes of the present invention to as follows: "partial or complete inhibiting, inhibition and/or retardation". In this case, it is within the specialist knowledge of the average person skilled in the art to measure and determine such inhibiting, inhibition, and/or retardation by means of the usual methods of measurement and determination. Thus, a partial inhibiting, inhibition and/or retardation, for example, can be measured and determined in relation to a complete inhibiting, inhibition and/or retardation.

The object of the present invention has surprisingly been solved in another aspect by providing a process for manufacturing a compound of the invention, comprising the steps of:

(a) reacting a compound of formula (III)

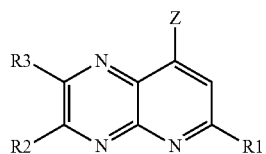
(III)

wherein
Z denotes Hal or B(OH)$_2$, and
R1, R2, R3 and Hal have the meaning as defined supra,
with a compound of formula (IVa), formula (IVb) or formula (V)

H—X-Het or (IVa)

Z'-Het or (IVb)

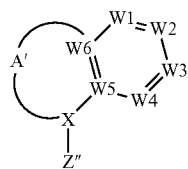
(V)

wherein
Z', Z" independently from each other denote Hal, boronic acid or a ester of boronic acid, and
X, Het, A', W1, W2, W3, W4, W5, W6 and Hal have the meaning as defined supra,
to yield the compound of formula (I) or formula (II)

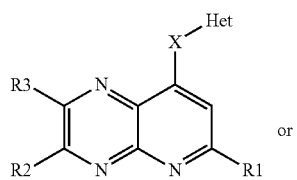
(I)

or

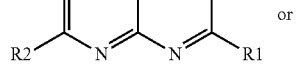

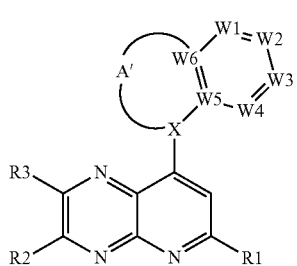
(II)

wherein
R1, R2, R3, X, Het, A', W1, W2, W3, W4, W5 and W6 have the meaning as defined supra,
or
(b) reacting a compound of formula (VI)

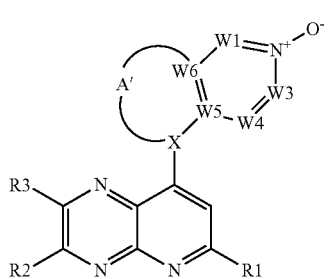
(VI)

wherein
R1, R2, R3, X, A', W1, W3, W4, W5 and W6 have the meaning as defined supra,
with alkyl- or arylsulfonylchloride, such as methanesulfonylchloride or p-toluenesulfonylchloride, pyridine or alkyl-pyridine and a primary alkylamine, such as ethanolamine or propylamine,
to yield a compound of formula (II') and/or formula (II")

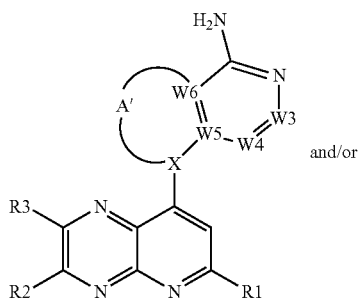
(II')

and/or

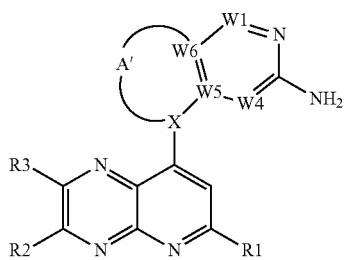
(II")

wherein
R1, R2, R3, X, A', W1, W3, W4, W5 and W6 have the meaning as defined supra,
and optionally
(c) converting a base or an acid of the compound of formula (I), formula (II), formula (II') or formula (II") into a salt thereof.

Some crude products were subjected to standard chromatography using solvent mixtures containing methanol, ethanol, isopropanol, n-hexane, cyclohexane, dichloromethane, n-heptane or petrol ether, respectively.

For a further detailed description of the manufacturing processes, please refer also to the examples and the following general description of the preferred conditions.

A physiologically acceptable salt of a compound of the invention can also be obtained by isolating and/or treating the compound of the invention obtained by the described reaction with an acid or a base.

The compounds of the invention and also the starting materials for their preparation are, are prepared by methods as described in the examples or by methods known per se, as described in the literature (for example in standard works, such as Houben-Weyl, Methoden der Organischen Chemie [Methods of Organic Chemistry], Georg Thieme Verlag, Stuttgart; Organic Reactions, John Wiley & Sons, Inc., New York), to be precise under reaction conditions which are known and suitable for the said reactions. Use can also be made here of variants which are known per se, but are not mentioned here in greater detail.

The starting materials for the claimed process may, if desired, also be formed in situ by not isolating them from the reaction mixture, but instead immediately converting them further into the compounds of the invention. On the other hand, it is possible to carry out the reaction stepwise.

Preferably, the reaction of the compounds is carried out in the presence of a suitable solvent, which is preferably inert under the respective reaction conditions. Examples of suitable solvents are hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, dimethylformamide (DMF) or N-methylpyrrolidinone (NMP); nitriles, such as acetonitrile; sulfoxides, such as dimethyl sulfoxide (DMSO); nitro compounds, such as nitromethane or nitrobenzene; esters, such as ethyl acetate, or mixtures of the said solvents or mixtures with water. Polar solvents are in general preferred. Examples for suitable polar solvents are chlorinated hydrocarbons, alcohols, glycol ethers, nitriles, amides and sulfoxides or mixtures thereof. More preferred are amides, especially dimethylformamide (DMF).

As stated above, the reaction temperature is between about −100° C. and 300° C., depending on the reaction step and the conditions used.

Reaction times are generally in the range between some minutes and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 min and 48 hrs.

A base of a compound of the invention can be converted into the associated acid-addition salt using an acid, for example by reaction of equivalent amounts of the base and the acid in a preferably inert solvent, such as ethanol, followed by evaporation. Suitable acids for this reaction are, in particular, those which give physiologically acceptable salts. Thus, it is possible to use inorganic acids, for example sulfuric acid, sulfurous acid, dithionic acid, nitric acid, hydrohalic acids, such as hydrochloric acid or hydrobromic acid, phosphoric acids, such as, for example, orthophosphoric acid, sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, hexanoic acid, octanoic acid, decanoic acid, hexadecanoic acid, octadecanoic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, trimethoxybenzoic acid, adamantanecarboxylic acid, p-toluenesulfonic acid, glycolic acid, embonic acid, chlorophenoxyacetic acid, aspartic acid, glutamic acid, proline, glyoxylic acid, palmitic acid, parachlorophenoxyisobutyric acid, cyclohexanecarboxylic acid, glucose 1-phosphate, naphthalenemono- and -disulfonic acids or laurylsulfuric acid.

Salts with physiologically unacceptable acids, for example picrates, can be used to isolate and/or purify the compounds of the invention.

On the other hand, compounds of the invention can be converted into the corresponding metal salts, in particular alkali metal salts or alkaline earth metal salts, or into the corresponding ammonium salts, using bases (for example sodium hydroxide, potassium hydroxide, sodium carbonate or potassium carbonate). Suitable salts are furthermore substituted ammonium salts, for example the dimethyl-, diethyl- and diisopropylammonium salts, monoethanol-, diethanol- and diisopropanolammonium salts, cyclohexyl- and dicyclohexylammonium salts, dibenzylethylenediammonium salts, furthermore, for example, salts with arginine or lysine.

If desired, the free bases of the compounds of the invention can be liberated from their salts by treatment with strong bases, such as sodium hydroxide, potassium hydroxide, sodium carbonate or potassium carbonate, so long as no further acidic groups are present in the molecule. In the cases where the compounds of the invention have free acid groups, salt formation can likewise be achieved by treatment with bases. Suitable bases are alkali metal hydroxides, alkaline earth metal hydroxides or organic bases in the form of primary, secondary or tertiary amines.

Every reaction step described herein can optionally be followed by one or more working up procedures and/or isolating procedures. Suitable such procedures are known in the art, for example from standard works, such as Houben-Weyl, Methoden der organischen Chemie [Methods of Organic Chemistry], Georg-Thieme-Verlag, Stuttgart). Examples for such procedures include, but are not limited to evaporating a solvent, distilling, crystallization, fractionised crystallization, extraction procedures, washing procedures, digesting procedures, filtration procedures, chromatography, chromatography by HPLC and drying procedures, especially drying procedures in vacuo and/or elevated temperature.

The object of the present invention has surprisingly been solved in another aspect by providing a medicament comprising at least one compound of the invention.

The object of the present invention has surprisingly been solved in another aspect by providing a medicament comprising at least one compound of the invention for use in the treatment and/or prophylaxis of physiological and/or pathophysiological conditions selected from the group consisting of: "cancer, tumour, malignant tumours, benign tumours, solid tumours, sarcomas, carcinomas, hyperproliferative disorders, carcinoids, Ewing sarcomas, Kaposi sarcomas, brain tumours, tumours originating from the brain and/or the nervous system and/or the meninges, gliomas, glioblastomas, neuroblastomas, stomach cancer, kidney cancer, kidney cell carcinomas, prostate cancer, prostate carcinomas, connective tissue tumours, soft tissue sarcomas, pancreas tumours, liver tumours, head tumours, neck tumours, laryngeal cancer, oesophageal cancer, thyroid cancer, osteosarcomas, retinoblastomas, thymoma, testicular cancer, lung cancer, lung adenocarcinoma, small cell lung carcinoma, bronchial carcinomas, breast cancer, mamma carcinomas, intestinal cancer, colorectal tumours, colon carcinomas, rectum carcinomas, gynaecological tumours, ovary tumours/ovarian tumours, uterine cancer, cervical cancer, cervix carcinomas, cancer of body of uterus, corpus carcinomas, endometrial carcinomas, urinary bladder cancer, urogenital tract cancer, bladder cancer, skin cancer, epithelial tumours, squamous epithelial carcinoma, basaliomas, spinaliomas, melanomas, intraocular melanomas, leukaemias, monocyte leukaemia, chronic leukaemias, chronic myelotic leukaemia, chronic lymphatic leukemia, acute leukaemias, acute myelotic leukaemia, acute lymphatic leukemia, lymphomas, opthalmic diseases, choroidal neovascularization, diabetic retinopathy, inflammatory diseases, arthritis, neurodegeneration, transplant rejection, metastatic growth, fibrosis, restenosis, HIV infection, atherosclerosis, inflammation and disorders of wound healing, angiogenesis, cardiovascular system, bone, CNS and/or PNS." A corresponding use for the preparation of a medicament for the treatment and/or prophylaxis of the aforementioned conditions is intended to be comprised. A corresponding method of treatment administering at least one compound of the invention to a patient in need thereof is also intended to be comprised.

Compounds of the invention may be used in combination with one or more other active substances (ingredients, drugs) in the treatment, prevention, suppression or amelioration of diseases or conditions for which compounds of the invention or the other substances have utility. Typically the combination of the drugs is safer or more effective than either drug alone, or the combination is safer or more effective than would it be expected based on the additive properties of the individual drugs. Such other drug(s) may be administered, by a route and in an amount commonly used contemporaneously or sequentially with a compound of the invention. When a compound of the invention is used contemporaneously with one or more other drugs, a combination product containing such other drug(s) and the compound of the invention is preferred. However, combination therapy also includes therapies in which the compound of the invention and one or more other drugs are administered on different overlapping schedules. It is contemplated that when used in combination with other active ingredients, the compound of the present invention or the other active ingredient or both may be used effectively in lower doses than when each is used alone. Accordingly, the pharmaceutical compositions of the present invention include those that contain one or more other active ingredients, in addition to a compound of the invention.

Examples of other active substances (ingredients, drugs) that may be administered in combination with a compound of the invention, and either administered separately or in the same pharmaceutical composition, include, but are not limited to the compounds classes and specific compounds listed in Table 1:

TABLE 1

| | | |
|---|---|---|
| Alkylating agents | Cyclophosphamide | Lomustine |
| | Busulfane | Procarbazine |
| | Ifosfamide | Altretamine |
| | Melphalane | Estramustinphosphate |
| | Hexamethylmelamine | Mechlorethamine |
| | Thiotepa | Streptozocine |
| | Chlorambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (AeternaZentaris) |
| | Carboxyphthalatoplatinum | Satraplatin (Johnson Matthey) |
| | Tetraplatin | BBR-3464 (Hoffmann-La |
| | Ormiplatin | Roche) |
| | Iproplatin | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycine |
| | 5-Fluoruracil | Fludarabine |
| | Floxuridine | Pentostatine |
| | 2-Chlordesoxyadenosine | Raltitrexede |
| | 6-Mercaptopurine | Hydroxyurea |
| | 6-Thioguanine | Decitabine (SuperGen) |
| | Cytarabine | Clofarabine (Bioenvision) |
| | 2-Fluordesoxycytidine | Irofulven (MGI Pharma) |
| | Methotrexate | DMDC (Hoffmann-La |
| | Idatrexate | Roche) |
| | | Ethinylcytidine (Taiho) |
| Topoisomerase inhibitors | Amsacrine | Rubitecane (SuperGen) |
| | Epirubicine | Exatecanmesylate (Daiichi) |
| | Etoposide | Quinamed (ChemGenex) |
| | Teniposide or Mitoxantrone | Gimatecane (Sigma-Tau) |
| | Irinotecane (CPT-11) | Diflomotecane (Beaufour-Ipsen) |
| | 7-Ethyl-10-hydroxycamptothecine | TAS-103 (Taiho) |

TABLE 1-continued

| | | |
|---|---|---|
| | Topotecane | Elsamitrucine (Spectrum) |
| | Dexrazoxanet (TopoTarget) | J-107088 (Merck & Co) |
| | Pixantrone (Novuspharma) | BNP-1350 (BioNumerik) |
| | Rebeccamycin-Analogue (Exelixis) | CKD-602 (Chong Kun Dang) |
| | | KW-2170 (Kyowa Hakko) |
| | BBR-3576 (Novuspharma) | |
| Antitumor antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |
| | Daunorubicin (Daunomycin) | Losoxantrone |
| | Epirubicin | Bleomycinsulfate (Blenoxan) |
| | Therarubicin | Bleomycinacid |
| | Idarubicin | Bleomycin A |
| | Rubidazone | Bleomycin B |
| | Plicamycinp | Mitomycin C |
| | Porfiromycin | MEN-10755 (Menarini) |
| | Cyanomorpholinodoxorubicin | GPX-100 (Gem Pharmaceuticals) |
| | Mitoxantron (Novantron) | |
| Antimitotic agents | Paclitaxel | SB 408075 (GlaxoSmithKline) |
| | Docetaxel | E7010 (Abbott) |
| | Colchicin | PG-TXL (Cell Therapeutics) |
| | Vinblastine | IDN 5109 (Bayer) |
| | Vincristine | A 105972 (Abbott) |
| | Vinorelbine | A 204197 (Abbott) |
| | Vindesine | LU 223651 (BASF) |
| | Dolastatine 10 (NCI) | D 24851 (ASTA Medica) |
| | Rhizoxine (Fujisawa) | ER-86526 (Eisai) |
| | Mivobuline (Warner-Lambert) | Combretastatine A4 (BMS) |
| | Cemadotine (BASF) | Isohomohalichondrin-B (PharmaMar) |
| | RPR 109881A (Aventis) | ZD 6126 (AstraZeneca) |
| | TXD 258 (Aventis) | PEG-Paclitaxel (Enzon) |
| | Epothilon B (Novartis) | AZ10992 (Asahi) |
| | T 900607 (Tularik) | !DN-5109 (Indena) |
| | T 138067 (Tularik) | AVLB (Prescient NeuroPharma) |
| | Cryptophycin 52 (Eli Lilly) | Azaepothilon B (BMS) |
| | Vinflunine (Fabre) | BNP-7787 (BioNumerik) |
| | Auristatine PE (Teikoku Hormone) | CA-4-Prodrug (OXiGENE) |
| | BMS 247550 (BMS) | Dolastatin-10 (NrH) |
| | BMS 184476 (BMS) | CA-4 (OXiGENE) |
| | BMS 188797 (BMS) | |
| | Taxoprexine (Protarga) | |
| Aromatase inhibitors | Aminoglutethimide | Exemestane |
| | Letrozole | Atamestane (BioMedicines) |
| | Anastrazole | YM-511 (Yamanouchi) |
| | Formestane | |
| Thymidylatesynthase inhibitors | Pemetrexed (Eli Lilly) | Nolatrexed (Eximias) |
| | ZD-9331 (BTG) | CoFactor ™ (BioKeys) |
| DNA antagonists | Trabectedine (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-Benzylguanine (Paligent) |
| | Thymectacine (NewBiotics) | |
| | Edotreotide (Novartis) | |
| Farnesyltransferase inhibitors | Arglabine (NuOncology Labs) | Tipifarnibe (Johnson & Johnson) |
| | lonafarnibe (Schering-Plough) | Perillylalcohol (DOR BioPharma) |
| | BAY-43-9006 (Bayer) | |
| Pump inhibitors | CBT-1 (CBA Pharma) | Zosuquidar-Trihydrochloride (Eli Lilly) |
| | Tariquidar (Xenova) | Biricodar-Dicitrate (Vertex) |
| | MS-209 (Schering AG) | |
| Histoneacetyltransferase inhibitors | Tacedinaline (Pfizer) | Pivaloyloxymethylbutyrate (Titan) |
| | SAHA (Aton Pharma) | Depsipeptide (Fujisawa) |
| | MS-275 (Schering AG) | |
| Metalloproteinase inhibitors/ | Neovastat (Aeterna Laboratories) | CMT-3 (CollaGenex) |
| | | BMS-275291 (Celltech) |
| Ribonucleosidereduktase inhibitors | Marimastat (British Biotech) | Tezacitabine (Aventis) |
| | Galliummaltolate (Titan) | Didox (Molecules for Health) |
| | Triapine (Vion) | |
| TNF-alpha agonists/ antagonists | Virulizine (Lorus Therapeutics) | Revimide (Celgene) |
| | CDC-394 (Celgene) | |

TABLE 1-continued

| | | |
|---|---|---|
| Endotheline-A receptor antagonists | Atrasentane (Abbot) ZD-4054 (AstraZeneca) | YM-598 (Yamanouchi) |
| Retinoic acid receptor agonists | Fenretinide (Johnson & Johnson) LGD-1550 (Ligand) | Alitretinoin (Ligand) |
| Immunomodulators | Interferon Oncophage (Antigenics) GMK (Progenics) Adenocarzinoma vaccine (Biomira) CTP-37 (AVI BioPharma) JRX-2 (Immuno-Rx) PEP-005 (Peplin Biotech) Synchrovax vaccine (CTL Immuno) Melanoma vaccine (CTL Immuno) p21-RAS vaccine (GemVax) | Dexosome therapy (Anosys) Pentrix (Australian Cancer Technology) JSF-154 (Tragen) Cancer vaccine (Intercell) Noreline (Biostar) BLP-25 (Biomira) MGV (Progenics) 13-Alethine (Dovetail) CLL-Thera (Vasogen) |
| Hormonal and anti-hormonal agents | Estrogens Conjugated Estrogens Ethinylestradiole Chlorotrianisen Idenestrole Hydroxyprogesteroncaproate Medroxyprogesterone Testosterone Testosteronpropionate Fluoxymesterone Methyltestosterone Diethylstilbestrole Megestrole Tamoxifen Toremofine Dexamethasone | Prednisone Methylprednisolone Prednisolone Aminoglutethimide Leuprolide Goserelin Leuporelin Cetrorelix Bicalutamide Flutamide Octreotide Nilutamide Mitotane P-04 (Novogen) 2-Methoxyestradiol (EntreMed) Arzoxifen (Eli Lilly) |
| Photodynamic agents | Talaporfine (Light Sciences) Theralux (Theratechnologies) Motexafin Gadolinium (Pharmacyclics) | Pd-Bacteriopheophorbide (Yeda) Lutetium-Texaphyrine (Pharmacyclics) Hypericine |
| Tyrosinkinase inhibitors | Imatinib (Novartis) Leflunomid (Sugen/Pharmacia) ZDl839 (AstraZeneca) Erlotinib (Oncogene Science) Canertjnib (Pfizer) Squalamin (Genaera) SU5416 (Pharmacia) SU6668 (Pharmacia) ZD4190 (AstraZeneca) ZD6474 (AstraZeneca) Vatalanib (Novartis) PKI166 (Novartis) GW2016 (GlaxoSmithKline) EKB-509 (Wyeth) EKB-569 (Wyeth) | Kahalid F (PharmaMar) CEP-701 (Cephalon) CEP-751 (Cephalon) MLN518 (Millenium) PKC412 (Novartis) Phenoxodiol O Trastuzumab (Genentech) C225 (ImClone) rhu-Mab (Genentech) MDX-H210 (Medarex) 2C4 (Genentech) MDX-447 (Medarex) ABX-EGF (Abgenix) IMC-1C11 (ImClone) |
| Different agents | SR-27897 (CCK-A inhibitor, Sanofi-Synthelabo) Tocladesine (cyclic-AMP agonist, Ribapharm) Alvocidib (CDK inhibitor, Aventis) CV-247 (COX-2-Inhibitor, Ivy Medical) P54 (COX-2 inhibitor, Phytopharm) CapCell ™ (CYP450 stimulans, Bavarian Nordic) GCS-IOO (gal3 antagonist, GlycoGenesys) G17DT immunogen (Gastrin inhibitor, Aphton) Efaproxiral (Oxygenator, Allos Therapeutics) PI-88 (Heparanase inhibitor, Progen) Tesmilifen (Histamine antagonist, YM BioSciences) Histamine (Histamine-H2 receptor agonist, Maxim) | BCX-1777 (PNP inhibitor, BioCryst) Ranpirnase (Ribonuclease stimulans, Alfacell) Galarubicin (RNA synthesis inhibitor, Dong-A) Tirapazamin (reducing agent, SRI International) N-Acetylcystein (reducing agent, Zambon) R-Flurbiprofen (NF-kappaB inhibitor, Encore) 3CPA (NF-kappaB inhibitor, Active Biotech) Seocalcitol (Vitamin-D receptor agonist, Leo) 131-I-TM-601 (DNA antagonist, TransMolecular) Eflornithin (ODC inhibitor, ILEX Oncology) Minodronic acid (Osteoclasts inhibitor, Yamanouchi) Indisulam (p53 stimulans, Eisai) |

TABLE 1-continued

| | |
|---|---|
| Tiazofurin (IMPDH inhibitor, Ribapharm) | Aplidin (PPT inhibitor, PharmaMar) |
| Cilengitide (Integrine antagonist, Merck KGaA) | Rituximab (CD20 antibody, Genentech) |
| SR-31747 (IL-1 antagonist, Sanofi-Synthelabo) | Gemtuzumab (CD33 antibody, Wyeth Ayerst) |
| CCI-779 (mTOR kinase inhibitor, Wyeth) | PG2 (Hematopoesis enhancer, Pharmagenesis) |
| Exisulind (PDE-V inhibitor, Cell Pathways) | Immunol ™ (Triclosan oral irrigation, Endo) |
| CP-461 (PDE-V inhibitor, Cell Pathways) | Triacetyluridine (Uridine prodrug, Wellstat) |
| AG-2037 (GART inhibitor, Pfizer) | SN-4071 (sarcoma agent, Signature BioScience) |
| WX-UK1 (Plasminogen activator inhibitor, Wilex) | TransMID-107 ™ (Immunotoxine, KS Biomedix) |
| PBI-1402 (PMN stimulans, ProMetic LifeSciences) | PCK-3145 (Apoptosis enhancer, Procyon) |
| Bortezomib (Proteasome inhibitor, Millennium) | Doranidazole (Apoptosis enhancer, Pola) |
| SRL-172 (T-cell stimulans, SR Pharma) | CHS-828 (cytotoxic agent, Leo) |
| TLK-286 (Glutathione-S-transferase inhibitor, Telik) | trans-Retinoic acid (Differentiator, NIH) |
| PT-100 (Growth factor agonist, Point Therapeutics) | MX6 (Apoptosis enhancer, MAXIA) |
| Midostaurin (PKC inhibitor, Novartis) | Apomin (Apoptosis enhancer, ILEX Oncology) |
| Bryostatin-1 (PKC stimulans, GPC Biotech) | Urocidine (Apoptosis enhancer, Bioniche) |
| CDA-II (Apoptosis enhancer, Everlife) | Ro-31-7453 (Apoptosis enhancer, La Roche) |
| SDX-101 (Apoptosis enhancer, Salmedix) | Brostallicin (Apoptosis enhancer, Pharmacia) |
| Ceflatonin (Apoptosis enhancer, ChemGenex) | |

In a preferred embodiment, a compound of the invention is administered in combination with one or more known anti-tumor agents, such as the following: estrogen receptor modulators, androgen receptor modulators, retinoid receptor modulators, cytotoxics, antiproliferative agents, prenyl proteintransferase inhibitors, HMG-CoA-reductase inhibitors, HIV protease inhibitors, reverse transcriptase inhibitors, angiogenesis inhibitors. The compounds of the present inventions are particularly suitable for administration at the same time as radiotherapy.

The compounds of the invention are in particular well suited for administration in combination with radiotherapy. The synergistic effects of VEGF inhibition in combination with radiotherapy are known to the skilled artisan (WO 00/61186).

The term "estrogen receptor modulators" in the course of the present invention refers to compounds that interfere with or inhibit the binding of estrogen to estrogen receptor—independently from the mode of action. Non-limiting examples of estrogen receptor modulators are tamoxifen, raloxifen, idoxifen, LY353381, LY 117081, toremifen, fulvestrant, 4-[7-(2, 2-Dimethyl-1-oxopropoxy-4-methyl-2-[4-[2-(1-piperidinyl) ethoxy]phenyl]-2H-1-benzopyran-3-yl]phenyl-2,2-dimethyl-propanoate, 4,4'-Dihydroxybenzophenon-2,4-dinitrophenylhydrazone and SH646.

The term "androgen receptor modulators" in the course of the present invention refers to compounds that interfere with or inhibit the binding of androgens to androgen receptor—independently from the mode of action. Non-limiting examples of androgen receptor modulators are finasteride and other 5alpha-reductase inhibitors, nilutamide, flutamide, bicalutamide, liarozole and abirateron acetate.

The term "retinoid receptor modulators" in the course of the present invention refers to compounds that interfere with or inhibit the binding of retinoids to retinoid receptor—independently from the mode of action. Non-limiting examples of retinoid receptor modulators are bexaroten, tretinoin, 13-cis-retinoic acid, 9-cis-retinoic acid, alpha-difluoromethylornithine, ILX23-7553, trans-N-(4'-Hydroxyphenyl)retinamide and N-4-carboxyphenylretinamide.

The term "cytotoxics" in the course of the present invention refers to compounds that primarily trigger cell death through direct action on cell function(s) or which interfere with or inhibit cell myosis, such as alkylating agents, tumor necrosis factors, intercalating agents, microtubule inhibitors and topoisomerase inhibitors. Non-limiting examples of cytotoxics are tirapazimin, sertenef, cachectine, ifosfamide, tasonermine, lonidamine, carboplatin, altretamine, prednimustine, dibromodulcit, ranimustine, fotemustine, nedaplatin, oxaliplatin, temozolomide, heptaplatin, estramustin, improsulfan-tosylate, trofosfamide, nimustine, dibrospidium-chloride, pumitepa, lobaplatin, satraplatin, profiromycin, cisplatin, irofulven, dexifosfamide, cis-amindichloro(2-methylpyridine)platin, benzylguanine, glufosfamide, GPX100, (trans, trans,trans)-bis-mu-(hexane-1,6-diamine)-mu-[diamine-platin(II)]bis-[diamine(chloro)platin(II)]-tetrachloride, diarizidinylspermine, arsenium trioxide, 1-(11-Dodecylamino-10-hydroxyundecyl)-3,7-dimethylxanthine, zorubicin, idarubicin, daunorubicin, bisantren, mitoxantron, pirarubicin, pinafide, valrubicine, amrubicine, antineoplaston, 3'-desamino-3'-morpholino-13-desoxo-10-hydroxycaminomycin, annamycin, galarubicin, elinafide, MEN10755 and 4-desmethoxy-3-desamino-3-aziridinyl-4-methylsulfonyl-daunorubicin (WO 00/50032).

Non-limiting examples of microtubule inhibitors are paclitaxel, vindesine-sulfate, 3',4'-dideshydro-4'-desoxy-8'-norvincaleukoblastine, docetaxol, rhizoxine, dolastatine, mivobuline-isethionate, auristatine, cemadotine, RPR109881, BMS184476, vinflunine, cryptophycine, 2,3,4,5,6-pentafluoro-N-(3-fluoro-4-methoxyphenyl)-benzenesulfonamide, anhydrovinblastine, N,N-dimethyl-L-valyl-L-valyl-N-methyl-L-valyl-L-prolyl-L-proline-t-butylamide, TDX258 and BMS188797.

Non-limiting examples of topoisomerase inhibitors are topotecane, hycaptamine, irinotecane, rubitecane, 6-ethoxypropionyl-3',4'-O-exo-benzylidene-chartreusine, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo-[de]-pyrano-[3',4':b,7]indolizino[1,2b]quiinoline-10,13(9H,15H)-dione, lurtotecane, 7-[2-(N-isopropylamino)ethyl]-(20S)camptothecine, BNP1350, BNPI1100, BN80915, BN80942, etoposide-phosphate, teniposide, sobuzoxane, 2'-dimethylamino-2'-desoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',':6,7)naphtho(2,3-d)-1,3-dioxol-6-one, 2,3-(methylendioxy)-5-methyl-7-hydroxy-8-methoxybenzo[c]phenanthridinium, 6,9-bis[(2-aminoethyl)amino]-benzo[g]isoquinoline-5,10-dione, 5-(3-aminopropylamino)-7,10-dihydroxy-2-(2-hydroxyethylaminomethyl)-6H-pyrazolo[4,5,1-de]-acridine-6-one, N-[1-[2(diethylamino)ethylamino]-7-methoxy-9-oxo-9H-thioxane-then-4-ylmethyl]formamide, N-(2-(dimethyl-amino)-ethyl)acridine-4-carboxamide, 6-[[2-(dimethylamino)-ethyl]amino]-3-hydroxy-7H-indeno[2,1-c]quinolin-7-one and dimesna.

Non-limiting examples of antiproliferative agents are antisense RNA- and antisense-DNA oligonucleotides, such as G3139, ODN698, RVASKRAS, GEM231 and INX3001, as well as antimetabolites such as enocitabine, carmofur, tegafur, pentostatine, doxifluridine, trimetrexate, fludarabine, capecitabine, galocitabine, cytarabin-ocfosfate, fosteabine sodiumhydrate, raltitrexed, paltitrexide, emitefur, tiazofurine, decitabine, nolatrexed, pemetrexed, nelzarabine, 2'-desoxy-2'-methylidencytidine, 2'-fluoromethylen-2'-desoxycytidine, N-[5-(2,3-dihydrobenzofuryl)sulfonyl]-N'-(3,4-dichlorophenyl)urea, N6-[4-desoxy-4-[N2-[2(E),4(E)-tetradecadienoyl]glycylamino]-L-glycero-B-L-manno-heptopyranosyl]adenine, aplidine, ecteinascidine, troxacitabine, 4-[2-amino-4-oxo-4,6,7,8-tetrahydro-3H-pyrimidino[5,4-b][1,4]thiazine-6-yl-(S)-ethyl]-2,5-thienoyl-L-glutaminic acid, aminopterine, 5-fluorouracil, alanosine, 11-acetyl-8-(carbamoyloxymethyl)-4-formyl-6-methoxy-14-oxa-1,11-diaza-tetracyclo-(7.4.1.0.0)-tetradeca-2,4,6-trien-9-ylacetic acid ester, swainsonine, lometrexole, dexrazoxane, methioninase, 2'-cyan-2'-desoxy-N4-palmitoyl-1-B-D-arabinofuranosylcytosine and 3-aminopyridine-2-carboxaldehyde-thiosemicarbazone.

"Antiproliferative agents" also comprises monoclonal antibodies against growth factors that have not been listed under "angiogenesis inhibitors", such as trastuzumab, as well as tumor suppressor genes, such as p53.

In another aspect of the invention, a medicament according to above aspects and embodiments is provided, wherein in such medicament comprises at least one additional pharmacologically active substance (drug, ingredient).

In a preferred embodiment the at least one pharmacologically active substance is a substance as described herein.

In another aspect of the invention, a medicament according to above aspects and embodiments is provided, wherein the medicament is applied before and/or during and/or after treatment with at least one additional pharmacologically active substance.

In a preferred embodiment the at least one pharmacologically active substance is a substance as described herein.

In another aspect of the invention, a pharmaceutical composition comprising a therapeutically effective amount of at least one compound of the invention is provided.

In a preferred embodiment, the pharmaceutical composition contains at least one additional compound selected from the group consisting of physiologically acceptable excipients, auxiliaries, adjuvants, diluents, carriers and/or additional pharmaceutically active substance other than the compounds of the invention.

In another aspect of the invention, a pharmaceutical composition is disclosed which comprises at least one compound of the invention, at least one pharmacologically active substance other than the compounds of the invention as described herein; and a pharmaceutically acceptable carrier.

A further embodiment of the present invention is a process for the manufacture of said pharmaceutical compositions, characterized in that one or more compounds according to the invention and one or more compounds selected from the group consisting of solid, liquid or semiliquid excipients, auxiliaries, adjuvants, diluents, carriers and pharmaceutically active agents other than the compounds according to the invention, are converted in a suitable dosage form.

In another aspect of the invention, a kit is provided comprising a therapeutically effective amount of at least one compound of the invention and/or at least one pharmaceutical composition as described herein and a therapeutically effective amount of at least one further pharmacologically active substance other than the compounds of the invention.

The pharmaceutical compositions of the present invention may be administered by any means that achieve their intended purpose. For example, administration may be by oral, parenteral, topical, enteral, intravenous, intramuscular, inhalant, nasal, intraarticular, intraspinal, transtracheal, transocular, subcutaneous, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired. Parenteral administration is preferred. Oral administration is especially preferred.

Suitable dosage forms include, but are not limited to capsules, tablets, pellets, dragees, semi-solids, powders, granules, suppositories, ointments, creams, lotions, inhalants, injections, cataplasms, gels, tapes, eye drops, solution, syrups, aerosols, suspension, emulsion, which can be produced according to methods known in the art, for example as described below:

tablets: mixing of active ingredient/s and auxiliaries, compression of said mixture into tablets (direct compression), optionally granulation of part of mixture before compression.

capsules: mixing of active ingredient/s and auxiliaries to obtain a flowable powder, optionally granulating powder, filling powders/granulate into opened capsules, capping of capsules.

semi-solids (ointments, gels, creams): dissolving/dispersing active ingredient/s in an aqueous or fatty carrier; subsequent mixing of aqueous/fatty phase with complementary fatty/aqueous phase, homogenization (creams only).

suppositories (rectal and vaginal): dissolving/dispersing active ingredient/s in carrier material liquified by heat (rectal: carrier material normally a wax; vaginal: carrier normally a heated solution of a gelling agent), casting said mixture into suppository forms, annealing and withdrawal suppositories from the forms.

aerosols: dispersing/dissolving active agent/s in a propellant, bottling said mixture into an atomizer.

In general, non-chemical routes for the production of pharmaceutical compositions and/or pharmaceutical preparations comprise processing steps on suitable mechanical means known in the art that transfer one or more compounds of the invention into a dosage form suitable for administration to a patient in need of such a treatment. Usually, the transfer of one or more compounds of the invention into such a dosage form comprises the addition of one or more compounds, selected from the group consisting of carriers, excipients, auxiliaries and pharmaceutical active ingredients other than the compounds of the invention. Suitable processing steps include, but are not limited to combining, milling, mixing, granulating, dissolving, dispersing, homogenizing, casting and/or compressing the respective active and non-active ingredients. Mechanical means for performing said processing steps are known in the art, for example from Ullmann's Encyclopedia of Industrial Chemistry, 5th Edition. In this respect, active ingredients are preferably at least one compound of the invention and one or more additional compounds other than the compounds of the invention, which show valuable pharmaceutical properties, preferably those pharmaceutical active agents other than the compounds of the invention, which are disclosed herein.

Particularly suitable for oral use are tablets, pills, coated tablets, capsules, powders, granules, syrups, juices or drops, suitable for rectal use are suppositories, suitable for parenteral use are solutions, preferably oil-based or aqueous solutions, furthermore suspensions, emulsions or implants, and suitable for topical use are ointments, creams or powders. The compounds of the invention may also be lyophilised and the resultant lyophilisates used, for example, for the preparation of injection preparations. The preparations indicated may be sterilised and/or comprise assistants, such as lubricants, preservatives, stabilisers and/or wetting agents, emulsifiers, salts for modifying the osmotic pressure, buffer substances, dyes, flavours and/or a plurality of further active ingredients, for example one or more vitamins.

Suitable excipients are organic or inorganic substances, which are suitable for enteral (for example oral), parenteral or topical administration and do not react with the compounds of the invention, for example water, vegetable oils, benzyl alcohols, alkylene glycols, polyethylene glycols, glycerol triacetate, gelatine, carbohydrates, such as lactose, sucrose, mannitol, sorbitol or starch (maize starch, wheat starch, rice starch, potato starch), cellulose preparations and/or calcium phosphates, for example tricalcium phosphate or calcium hydrogen phosphate, magnesium stearate, talc, gelatine, tragacanth, methyl cellulose, hydroxypropylmethylcellulose, sodium carboxymethylcellulose, polyvinyl pyrrolidone and/or vaseline.

If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries include, without limitation, flow-regulating agents and lubricants, for example, silica, talc, stearic acid or salts thereof, such as magnesium stearate or calcium stearate, and/or polyethylene glycol. Dragee cores are provided with suitable coatings, which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices or to provide a dosage form affording the advantage of prolonged action, the tablet, dragee or pill can comprise an inner dosage and an outer dosage component me latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, acetyl alcohol, solutions of suitable cellulose preparations such as acetyl-cellulose phthalate, cellulose acetate or hydroxypropylmethyl-cellulose phthalate, are used. Dye stuffs or pigments may be added to the tablets or dragee coatings, for example, for identification or in order to characterize combinations of active compound doses.

Suitable carrier substances are organic or inorganic substances which are suitable for enteral (e.g. oral) or parenteral administration or topical application and do not react with the novel compounds, for example water, vegetable oils, benzyl alcohols, polyethylene glycols, gelatin, carbohydrates such as lactose or starch, magnesium stearate, talc and petroleum jelly. In particular, tablets, coated tablets, capsules, syrups, suspensions, drops or suppositories are used for enteral administration, solutions, preferably oily or aqueous solutions, furthermore suspensions, emulsions or implants, are used for parenteral administration, and ointments, creams or powders are used for topical application. The compounds of the invention can also be lyophilized and the lyophilizates obtained can be used, for example, for the production of injection preparations.

The preparations indicated can be sterilized and/or can contain excipients such as lubricants, preservatives, stabilizers and/or wetting agents, emulsifiers, salts for affecting the osmotic pressure, buffer substances, colorants, flavourings and/or aromatizers. They can, if desired, also contain one or more further active compounds, e.g. one or more vitamins.

Other pharmaceutical preparations, which can be used orally include push-fit capsules made of gelatine, as well as soft, sealed capsules made of gelatine and a plasticizer such as glycerol or sorbitol. The push-fit capsules can contain the active compounds in the form of granules, which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

The liquid forms in which the novel compositions of the present invention may be incorporated for administration orally include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatine.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400).

Aqueous injection suspensions may contain substances, which increase the viscosity of the suspension, including, for example, sodium carboxymethyl cellulose, sorbitol, and/or dextran, optionally, the suspension may also contain stabilizers.

For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronized form, in which case one or more additional physiologically acceptable solvents may be present, for example ethanol. Inhalation solutions can be administered with the aid of conventional inhalers.

Possible pharmaceutical preparations, which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatine rectal capsules, which consist of a combination of the active compounds with a base. Possible base materials include, for example, liquid triglycerides, polyethylene glycols, or paraffin hydrocarbons.

For use in medicine, the compounds of the present invention will be in the form of pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic bases, e.g. quaternary ammonium salts.

The pharmaceutical preparations can be employed as medicaments in human and veterinary medicine. As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. Said therapeutic effective amount of one or more of the compounds of the invention is known to the skilled artisan or can be easily determined by standard methods known in the art.

The compounds of the invention and the additional active substances are generally administered analogously to commercial preparations. Usually, suitable doses that are therapeutically effective lie in the range between 0.0005 mg and 1000 mg, preferably between 0.005 mg and 500 mg and especially between 0.5 mg and 100 mg per dose unit. The daily dose is preferably between about 0.001 mg/kg and 10 mg/kg of body weight.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For the purpose of the present invention, all mammalian species are regarded as being comprised. In a preferred embodiment, such mammals are selected from the group consisting of "primate, human, rodent, equine, bovine, canine, feline, domestic animals, cattle, livestock, pets, cow, sheep, pig, goat, horse, pony, donkey, hinny, mule, hare, rabbit, cat, dog, guinea pig, hamster, rat, mouse". More preferably, such mammals are humans. Animal models are of interest for experimental investigations, providing a model for treatment of human diseases.

The specific dose for the individual patient depends, however, on the multitude of factors, for example on the efficacy of the specific compounds employed, on the age, body weight, general state of health, the sex, the kind of diet, on the time and route of administration, on the excretion rate, the kind of administration and the dosage form to be administered, the pharmaceutical combination and severity of the particular disorder to which the therapy relates. The specific therapeutic effective dose for the individual patient can readily be determined by routine experimentation, for example by the doctor or physician, which advises or attends the therapeutic treatment.

In the case of many disorders, the susceptibility of a particular cell to treatment with the subject compounds may be determined by in vitro testing. Typically a culture of the cell is combined with a subject compound at varying concentrations for a period of time sufficient to allow the active agents to show a relevant reaction, usually between about one hour and one week. For in vitro testing, cultured cells from a biopsy sample may be used.

Even without further details, it is assumed that a person skilled in the art will be able to utilise the above description in the broadest scope. The preferred embodiments should therefore merely be regarded as descriptive disclosure, which is absolutely not limiting in any way.

Above and below, all temperatures are indicated in ° C. In the following examples, "conventional work-up" means that, if necessary, the solvent is removed, water is added if necessary, the pH is adjusted, if necessary, to between 2 and 10, depending on the constitution of the end product, the mixture is extracted with ethyl acetate or dichloromethane, the phases are separated, the organic phase is washed with saturated $NaHCO_3$ solution, if desired with water and saturated NaCl solution, is dried over sodium sulfate, filtered and evaporated, and the product is purified by chromatography on silica gel, by preparative HPLC and/or by crystallisation. The purified compounds are, if desired, freeze-dried.

HPLC/MS Conditions A:

column: Chromolith SpeedROD RP-18e, 50×4.6 mm$^2$ gradient: A:B=96:4 to 0:100 flow rate: 2.4 ml/min eluent A: water+0.05% formic acid eluent B: acetonitrile+0.04% formic acid wavelength: 220 nm mass spectroscopy: positive mode HPLC/MS Conditions B:

column: Chromolith PerformanceROD RP-18e, 100×3 mm² gradient: A:B=99:1 to 0:100 flow rate: 2.0 ml/min eluent A: water+0.05% formic acid eluent B: acetonitrile+0.04% formic acid wavelength: 220 nm mass spectroscopy: positive mode Mass spectrometry (MS): ESI (electrospray ionisation) (M+H)+

LIST OF ABBREVIATIONS AND ACRONYMS

AcOH acetic acid, anh anhydrous, atm atmosphere(s), BOC tert-butoxycarbonyl CDI 1,1'-carbonyl diimidazole, conc concentrated, d day(s), dec decomposition, DIAD diisopropyl azodicarboxylate, DMAC NN-dimethylacetamide, DMPU 1,3-dimethyl-3,4,5,6-tetrahydro-2(1H)-pyrimidinone, DMF NN-dimethylformamide, DMSO dimethylsulfoxide, DPPA diphenylphosphoryl azide, EDCI 1-(3-dimethylaminopropyl)-3-ethylcarbodiimide, EtOAc ethyl acetate, EtOH ethanol (100%), Et₂O diethyl ether, Et₃N triethylamine, h hour(s), MeOH methanol, pet. ether petroleum ether (boiling range 30-60° C.), PPh₃ triphenylphospine, temp. temperature, THF tetrahydrofuran, TFA trifluoroAcOH, Tf trifluoromethanesulfonyl.

The contents of all cited references are hereby incorporated by reference in their entirety. The invention is explained in more detail by means of the following examples without, however, being restricted thereto.

EXAMPLES

I. Synthesis of Selected Compounds of the Invention

The following compounds were synthesized and characterized. However, it lies in the knowledge of a person skilled in the art to prepare and characterize these compounds differently.

Example 1

Synthesis of Compound 1

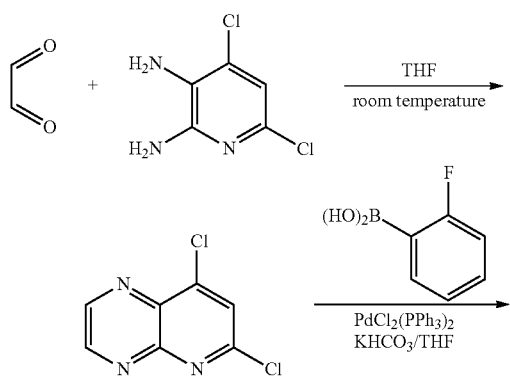

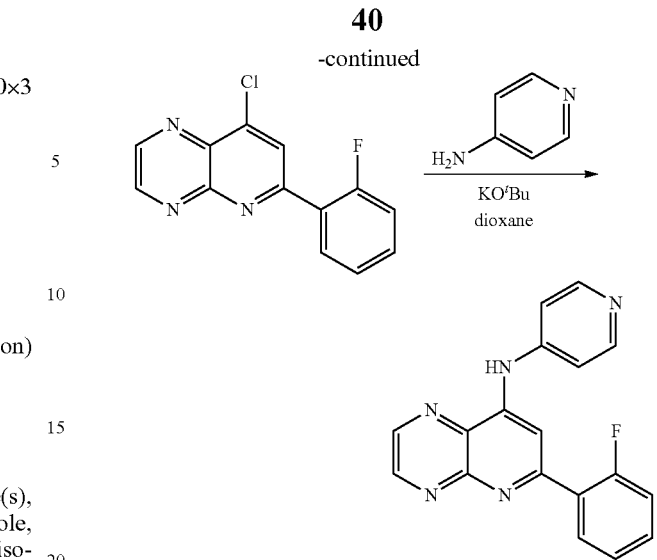

1. A solution of 4.81 g (27 mmol) 4,6-dichloro-pyridine-2,3-diamine (synthesis described in J. E. Schelling, C. A. Salemink, Rec. Tray. Chim. Pays-Bas 91, 650 [1972]) in 50 ml THF was treated with 5.22 g (27 mmol) of a 30% solution of glyoxal in water and the mixture was stirred for 3 days at room temperature. The reaction mixture was evaporated and the residue was partitioned between dichloromethane and diluted sodium carbonate solution. The organic phase was dried over sodium sulfate and evaporated. The residue was chromatographed on a silica gel column with cyclohexane/ethyl acetate as eluent yielding 6,8-dichloro-pyrido[2,3-b]pyrazine as off-white fine needles; HPLC/MS (B): 1.93 min, [M+H] 200.

$^1$H NMR (400 MHz, CDCl₃) δ=9.16 (d, J=1.7, 1H), 9.05 (d, J=1.7, 1H), 7.89 (s, 1H).

2. A solution of 1.60 g (8.00 mmol) 6,8-dichloro-pyrido[2,3-b]pyrazine, 1.12 g (8.00 mmol) 2-fluorophenylboronic acid and 961 mg (9.60 mmol) potassium hydrogen carbonate in 16 ml THF and 1.6 ml water was heated to 80° C. under nitrogen. Then 112 mg (0.16 mmol) bis-(triphenylphosphine)-palladium(II)-chloride were added and the mixture was stirred for 16 hrs at 80° C. Water was added to the reaction mixture and the precipitate was filtered off, dried in vacuum and recrystallized from 2-propanol: 8-chloro-6-(2-fluoro-phenyl)-pyrido[2,3-b]pyrazine as slightly yellow crystals; HPLC/MS (B): 2.68 min, [M+H] 260.

$^1$H NMR (400 MHz, CDCl₃) δ=9.08 (d, J=1.7, 1H), 8.96 (d, J=1.7, 1H), 8.36 (d, J=1.4, 1H), 8.27 (td, J=7.9, 1.8, 1H), 7.45 (m, 1H), 7.28 (m, 1H), 7.17 (ddd, J=11.6, 8.3, 0.8, 1H).

3. A solution of 52.2 mg (0.20 mmol) 8-chloro-6-(2-fluoro-phenyl)-pyrido[2,3-b]pyrazine in 1 ml dioxane was heated to 80° C. under nitrogen. Then 20.7 mg (0.22 mmol) 4-aminopyridine and 47.3 mg (0.42 mmol) potassium-tert-butoxide were added and the mixture was stirred at the same temperature for 5 minutes. Water was added to the reaction mixture. The resulting precipitate was filtered off and washed with water. The filtrate was extracted several times with dichloromethane; the organic phase was dried over sodium sulphate and evaporated. The residue was combined with the filtrate and purified by preparative HPLC. The fractions containing product were evaporated and partitioned between sodium hydrogen carbonate solution and dichloromethane. The organic phase was dried over sodium sulphate and evaporated yielding [6-(2-fluoro-phenyl)-pyrido[2,3-b]pyrazin-8-yl]-pyridin-4-yl-amine as yellow crystals HPLC/MS (A): 1.37 min, [M+H] 318.

¹H NMR (400 MHz, DMSO) δ=10.06 (s, 1H), 9.19 (d, J=1.8, 1H), 8.99 (d, J=1.8, 1H), 8.50 (m, 2H), 8.11 (td, J=8.0, 1.9, 1H), 7.97 (d, J=1.5, 1H), 7.58 (m, 3H), 7.41 (m, 2H).

Compounds 2 and 14 were prepared similarly.

Example 2

Synthesis of Compound 3

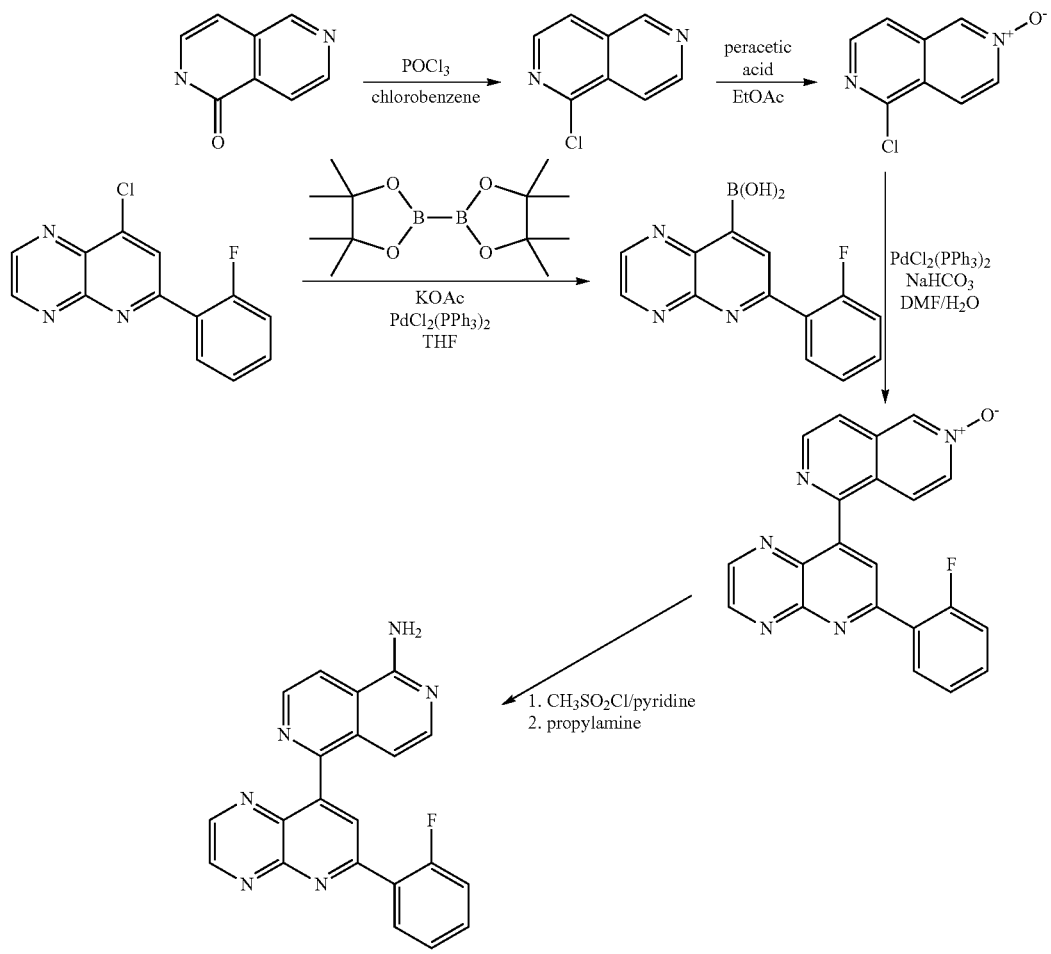

1. Under stirring, 184 ml (2.00 mol) phosphorus oxychloride was added slowly to a suspension of 146 g (1.00 mol) 2,6-naphthyridine-1(2H)-one in 1500 ml chlorobenzene at room temperature. The reaction mixture was heated to 100° C., stirred at this temperature for 16 hours and then cooled to room temperature. The solids were filtered off, washed with chlorobenzene and dried under vacuum. The residue was taken up in 1.5 l ice-cold water, 350 ml 50% aqueous sodium hydroxide solution to reach a pH value of 7-8. The precipitate thus formed was filtered off, washed with water and dried under vacuum yielding 1-chloro-[2,6]naphthyridine as brown crystals; HPLC/MS (A): 1.62 min, [M+H] 165.

¹H NMR (400 MHz, DMSO) δ=9.54 (d, J=0.8, 1H), 8.86 (d, J=5.9, 1H), 8.54 (d, J=5.6, 1H), 8.11 (dd, J=5.6, 0.8, 1H), 8.07 (d, J=5.9, 1H).

2. Under stirring, 205 ml (1.2 mol) peracetic acid (39% solution in acetic acid) was added to a solution of 98.8 g (0.60 mol) 1-chloro-[2,6]naphthyridine in 500 ml ethyl acetate and the mixture was stirred 18 hours at room temperature. The reaction mixture was diluted with water and acetic acid, treated with portions of sodium disulfite under stirring until a peroxide test was negative. Then the mixture was adjusted to pH value of 8 with aqueous NaOH. The solids were filtered off, washed with water and dried yielding 1-chloro-[2,6]-naphthyridine 6-oxide as slightly yellow crystals. The organic phase of the filtrate was separated, dried over sodium sulfate and evaporated. The residue was crystallized from tert-butyl-methyl-ether yielding another crop of product. HPLC/MS (A): 1.16 min, [M+H] 181.

¹H NMR (400 MHz, DMSO) δ=9.00 (d, J=1.8, 1H), 8.33 (d, J=5.7, 1H), 8.28 (dd, J=7.3, 1.8, 1H), 8.04 (d, J=7.3, 1H), 7.71 (d, J=5.6, 1H).

3. A suspension of 1.30 g (5.00 mmol) 8-chloro-6-(2-fluoro-phenyl)-pyrido[2,3-b]pyrazine, 1.65 g (6.50 mmol) bis-pinacolato-diboron and 1.47 g (15 mmol) dry potassium acetate in 20 ml THF was heated to 80° C. under nitrogen. Then 70 mg (0.10 mmol) bis-(triphenylphosphine)-palladium(II)-chloride was added and the reaction mixture was stirred for 16 hours at 80° C. The mixture was cooled to room temperature and water was added. The resulting precipitate was filtered off, washed with water and dried under vacuum yielding [6-(2-fluorophenyl)pyrido[2,3-b]pyrazin-8-yl]-boronic acid as dark grey solid; HPLC/MS (A): 1.72 min, [M+H] 270.

¹H NMR (400 MHz, DMSO) δ=9.23 (d, J=1.8, 1H), 9.10 (d, J=1.8, 1H), 9.06 (s, 2H), 8.44 (d, J=2.5, 1H), 8.10 (td, J=7.8, 1.6, 1H), 7.63 (m, 1H), 7.44 (m, 2H).

4. A suspension of 120 mg (0.45 mmol) [6-(2-fluorophenyl)pyrido[2,3-b]pyrazin-8-yl]boronic acid, 73 mg (0.41 mmol) 1-chloro-[2,6]-naphthyridine 6-oxide and 41 mg (0.49 mmol) sodium hydrogen carbonate in 1 ml DMF and 0.5 ml water was heated to 50° C. under nitrogen. Then 5.7 mg (0.008 mmol) bis-(triphenylphosphine)-palladium(II)-chloride was added. The reaction mixture was stirred for 16 hours at 80° C. Water was added and the resulting precipitate was filtered off, washed with water and dried under vacuum yielding 6-(2-fluoro-phenyl)-8-(6-oxy-[2,6]naphthyridin-1-yl)-pyrido[2,3-b]pyrazine as light brown solid; HPLC/MS (A): 1.61 min, [M+H] 370.

5. 40 mg (0.35 mmol) methanesulfonyl chloride was added slowly to a suspension of 107 mg (0.29 mmol) 6-(2-fluoro-phenyl)-8-(6-oxy-[2,6]naphthyridin-1-yl)-pyrido[2,3-b]pyrazine in 0.9 ml pyridine and the reaction mixture was stirred for 90 minutes at room temperature. Then 430 mg (7.27 mmol) propylamine were added and the mixture was stirred for another 90 minutes at room temperature. The reaction mixture was partitioned between water and dichloromethane. The organic phase was dried over sodium sulfate and evaporated. The residue was chromatographed on a silica gel column with dichloromethane/methanol as eluent yielding 5-[6-(2-Fluoro-phenyl)-pyrido[2,3-b]pyrazin-8-yl]-[2,6]naphthyridin-1-ylamine as light brown crystals; HPLC/MS (A): 1.45 min, [M+H] 369.

¹H NMR (400 MHz, DMSO) δ=9.20 (d, J=1.7, 1H), 8.91 (d, J=1.7, 1H), 8.71 (d, J=5.8, 1H), 8.31 (d, J=2.2, 1H), 8.25 (dd, J=5.8, 0.8, 1H), 8.21 (td, J=7.9, 1.8, 1H), 7.77 (d, J=6.0, 1H), 7.64 (m, 1H), 7.46 (m, 2H), 7.26 (s, 2H), 6.33 (dd, J=6.0, 0.8, 1H).

Compounds 5 and 8 were prepared similarly.

Compound 4 was prepared similarly according to the following reaction scheme:

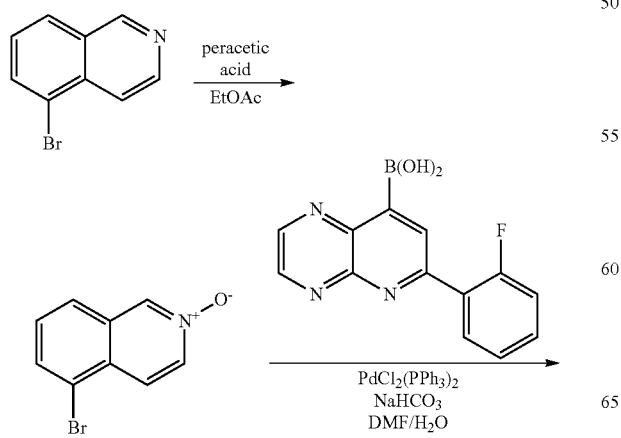

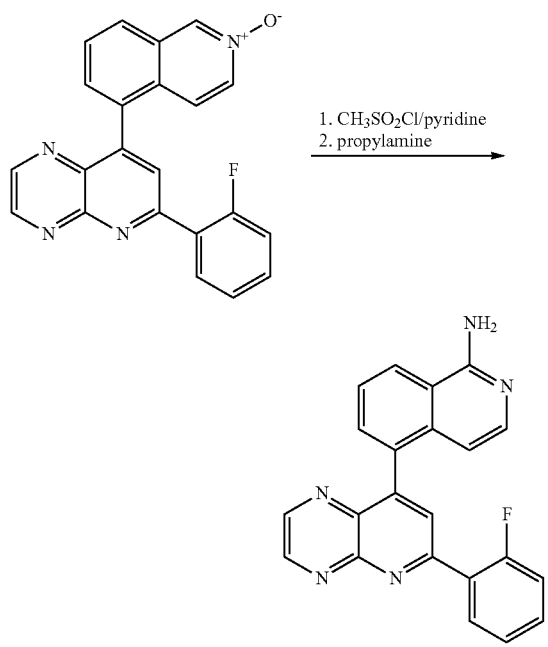

Example 3

Synthesis of Compound 6

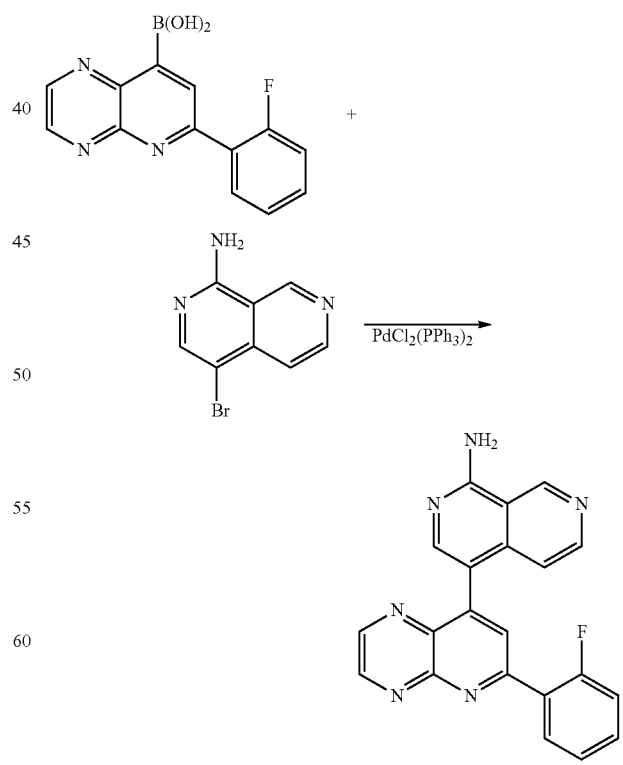

The reaction was performed similar to example 2, step 4.

Example 4
Synthesis of Compound 7
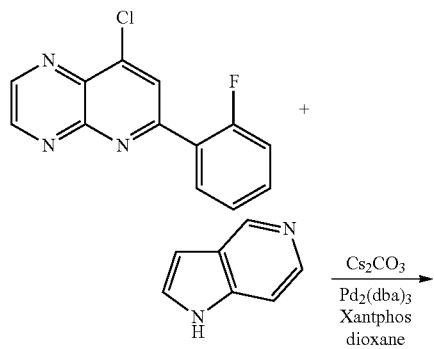
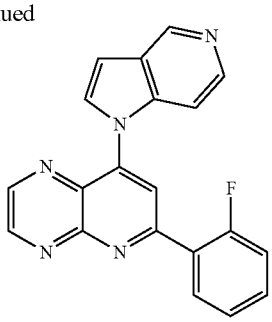
The reaction can be performed similar to a literature procedure: J. Yin, S. L. Buchwald, J. Am. Chem. Soc. 2002, 124, 6043-6048.
Example 5
Synthesis of Compound 10
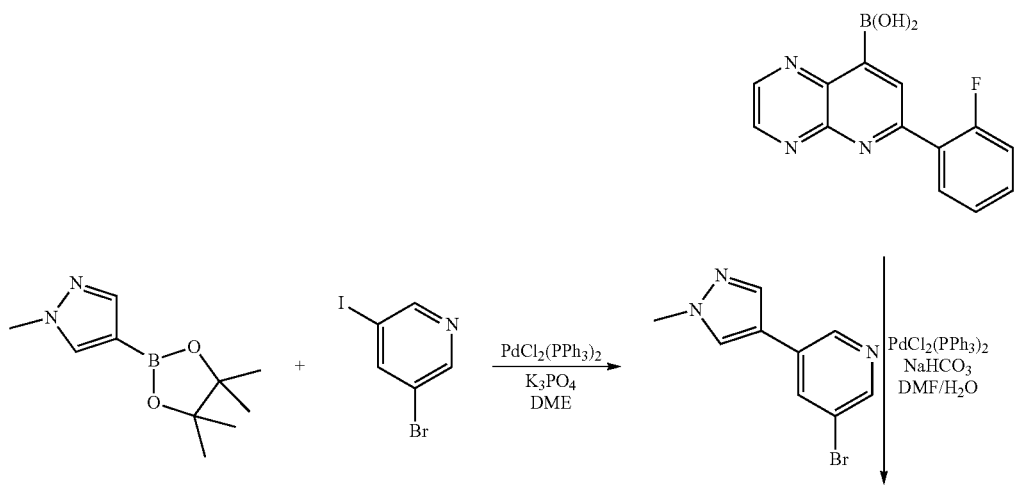
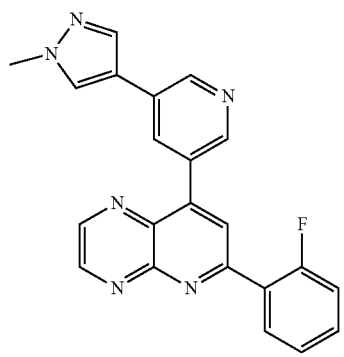

1. A suspension of 5.68 g (20.0 mmol) 3-bromo-5-iodo-pyridine, 4.37 g (21.0 mmol) 1-methyl-4-(4,4,5,5-tetramethyl-[1,3,2]dioxaborolan-2-yl)-1H-pyrazol and 8.49 g (40.0 mmol) tri-potassium-phosphate-trihydrate in 40 ml 1,2-dimethoxyethane was heated to 80° C. under nitrogen. Then 281 mg (0.40 mmol) bis-(triphenylphosphine)-palladium(II)-chloride were added. The reaction mixture was stirred for 16 hours at 80° C. The reaction mixture was cooled to room temperature and partitioned between water and dichloromethane. The organic phase was dried over sodium sulphate and evaporated. The residue was chromatographed on a silica gel column with dichloromethane/methanol as eluent yielding 3-bromo-5-(1-methyl-1H-pyrazol-4-yl)-pyridine as colourless crystals; HPLC/MS (A): 1.77 min, [M+H] 238/240.

2. A suspension of 119 mg (0.50 mmol) 3-bromo-5-(1-methyl-1H-pyrazol-4-yl)-pyridine, 148 mg (0.55 mmol) [6-(2-fluorophenyl)pyrido[2,3-b]pyrazin-8-yl]-boronic acid and 7.0 mg (0.01 mmol) bis-(triphenylphosphine)-palladium(II)-chloride in 1 ml DMF was heated to 80° C. under nitrogen. Then a solution of 50 mg (0.60 mmol) sodium hydrogen carbonate in 0.5 ml water was added and the reaction mixture was stirred for 18 hours at 80° C. The reaction mixture was cooled to room temperature. Water was added and the resulting precipitate was filtered off, washed with water and dried under vacuum. The residue was chromatographed on a silica gel column with dichloromethane/methanol as eluent yielding 6-(2-fluoro-phenyl)-8-[5-(1-methyl-1H-pyrazol-4-yl)-pyridin-3-yl]-pyrido[2,3-b]pyrazine as off-white solid; HPLC/MS (B): 2.27 min, [M+H] 383.

$^1$H NMR (500 MHz, DMSO) δ=9.24 (d, J=1.7, 1H), 9.12 (d, J=1.7, 1H), 8.98 (d, J=2.1, 1H), 8.84 (d, J=2.0, 1H), 8.41 (m, 2H), 8.34 (s, 1H), 8.16 (td, J=8.0, 1.8, 1H), 8.05 (s, 1H), 7.66 (m, 1H), 7.48 (m, 2H), 3.91 (s, 3H).

Compound 11 can be prepared similarly.

Example 6

Synthesis of Compound 9

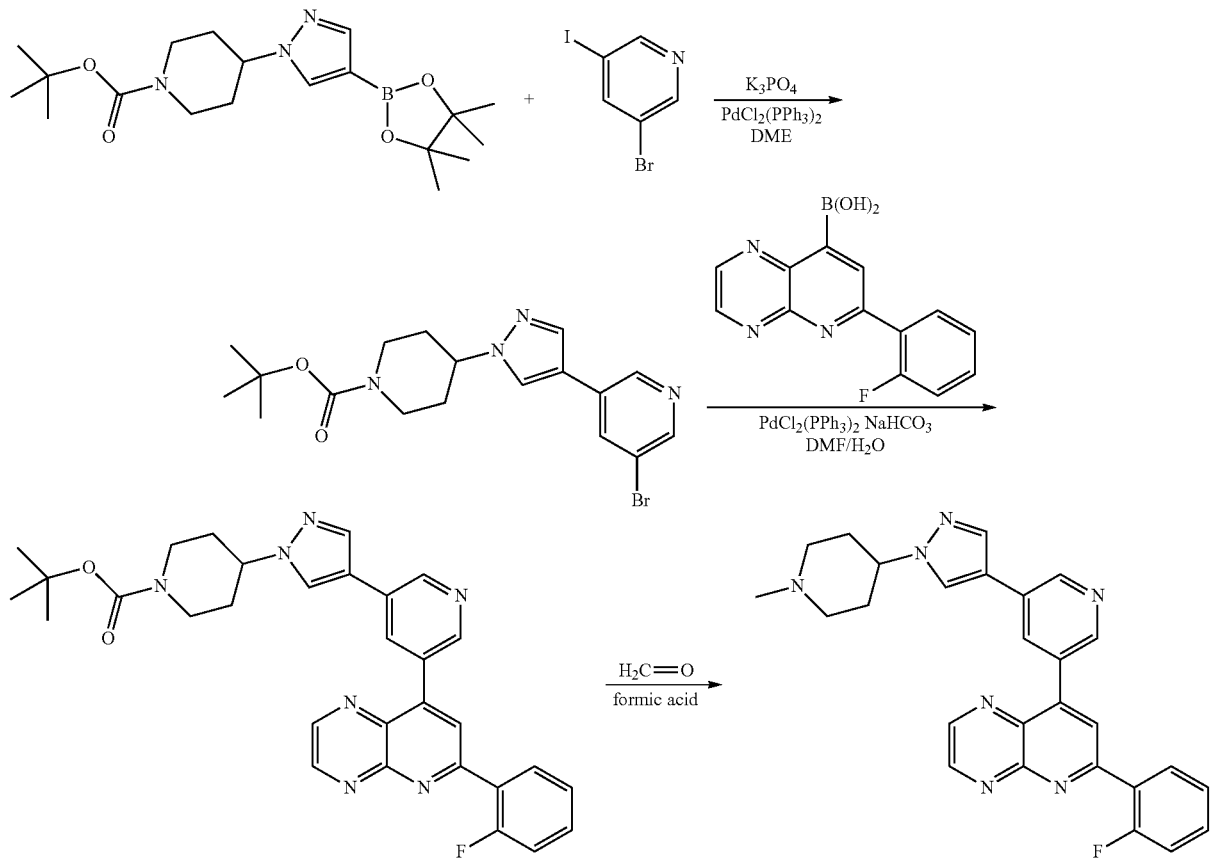

1. A suspension of 5.68 g (20.0 mmol) 3-bromo-5-iodo-pyridine, 7.55 g (20.0 mmol) 4-[4-(4,4,5,5-tetramethyl-[1,3,2]dioxaborolan-2-yl)-pyrazol-1-yl]-piperidin-1-carboxylic acid tert-butyl ester (synthesis described in WO 2007/066187) and 8.49 g (40.0 mmol) tri-potassium-phosphate-trihydrate in 40 ml 1,2-dimethoxyethane was heated to 80° C. under nitrogen. Then 421 mg (0.60 mmol) bis-(triphenylphosphine)-palladium(II)-chloride and 50 µl (0.361 mmol) triethylamine were added. The reaction mixture was stirred for 16 hours at 80° C. The reaction mixture was partitioned between THF and saturated sodium chloride solution. The organic phase was dried over sodium sulfate and evaporated. The residue was recrystallized from isopropanol yielding 4-[4-(5-bromo-pyridin-3-yl)-pyrazol-1-yl]-piperidine-1-carboxylic acid tert-butyl-ester as slightly yellow crystals; HPLC-MS (A): 2.41 min, [M+H] 407/409.

2. A suspension of 296 mg (0.73 mmol) 4-[4-(5-bromo-pyridin-3-yl)-pyrazol-1-yl]-piperidine-1-carboxylic acid tert-butyl-ester, 215 mg (0.80 mmol) [6-(2-fluorophenyl)pyrido[2,3-b]pyrazin-8-yl]-boronic acid and 10 mg (0.015 mmol) bis-(triphenylphosphine)-palladium(II)-chloride in 1.5 ml DMF water was heated to 80° C. under nitrogen. Then a solution of 73 mg (0.87 mmol) sodium hydrogen carbonate in 0.75 ml water was added. The reaction mixture was stirred for 20 hours at 80° C. The reaction mixture was cooled to room temperature. Water was added, the resulting precipitate was filtered off, washed with water and dried under vacuum. The residue was chromatographed on a silica gel column with dichloromethane/methanol as eluent yielding 4-(4-{5-[6-(2-fluoro-phenyl)-pyrido[2,3-b]pyrazin-8-yl]-pyridin-3-yl}-pyrazol-1-yl)-piperidine-1-carboxylic acid tert-butyl ester as off-white solid crystals; HPLC-MS (A): 2.37 min, [M+H] 552.

3. A solution of 85 mg (0.15 mmol) 4-(4-{5-[6-(2-fluoro-phenyl)-pyrido[2,3-b]pyrazin-8-yl]-pyridin-3-yl}-pyrazol-1-yl)-piperidine-1-carboxylic acid tert-butyl ester in 0.5 ml formic acid was treated with 36 µl (0.45 mmol) 35% aqueous formaldehyde solution and heated to 80° C. The reaction mixture was stirred at this temperature for 4 hours. The volume of the reaction mixture was reduced under vacuum and 2 N aqueous NaOH was added. The resulting precipitate was filtered off, washed with water and dried. The residue was chromatographed on a silica gel column with dichloromethane/methanol as eluent yielding 6-(2-fluoro-phenyl)-8-{5-[1-(1-methyl-piperidin-4-yl)-1H-pyrazol-4-yl]-pyridin-3-yl}-pyrido[2,3-b]pyrazine as off-white solid; HPLC/MS: 1.47 min, [M+H] 466.

$^1$H NMR (400 MHz, DMSO) δ=9.24 (d, J=1.7, 1H), 9.12 (d, J=1.7, 1H), 8.99 (d, J=2.1, 1H), 8.82 (d, J=2.0, 1H), 8.45 (s, 1H), 8.41 (t, J=2.1, 1H), 8.40 (d, J=2.1, 1H), 8.15 (td, J=8.0, 1.9, 1H), 8.06 (s, 1H), 7.65 (m, 1H), 7.47 (m, 2H), 4.14 (m, 1H), 2.86 (d, J=11.3, 2H), 2.21 (s, 3H), 2.02 (m, 6H).

Example 7

Synthesis of Compound 12

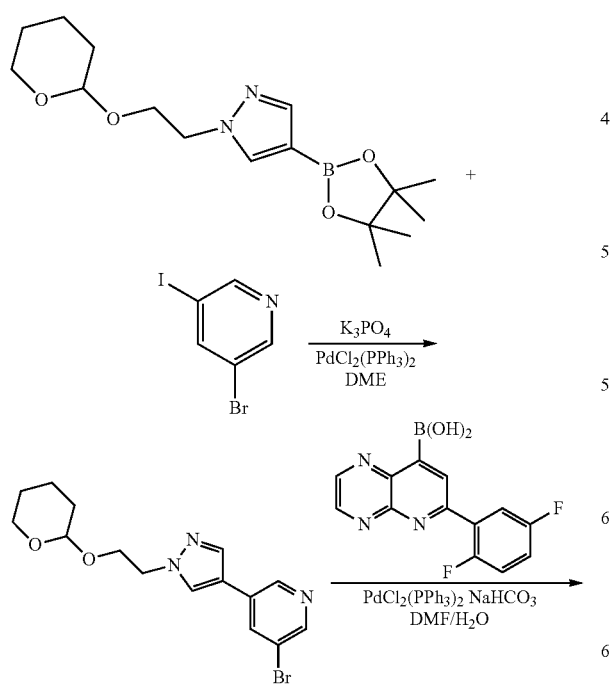

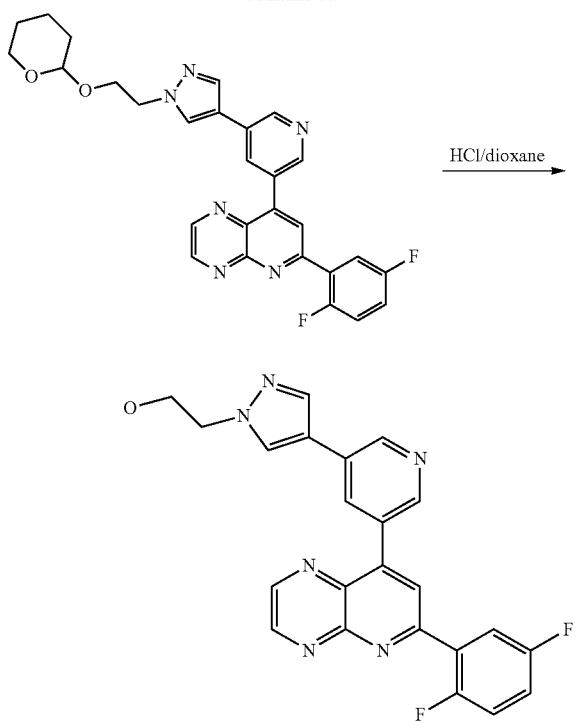

The synthesis can be performed similarly to example 2.

Example 8

Synthesis of Compound 13

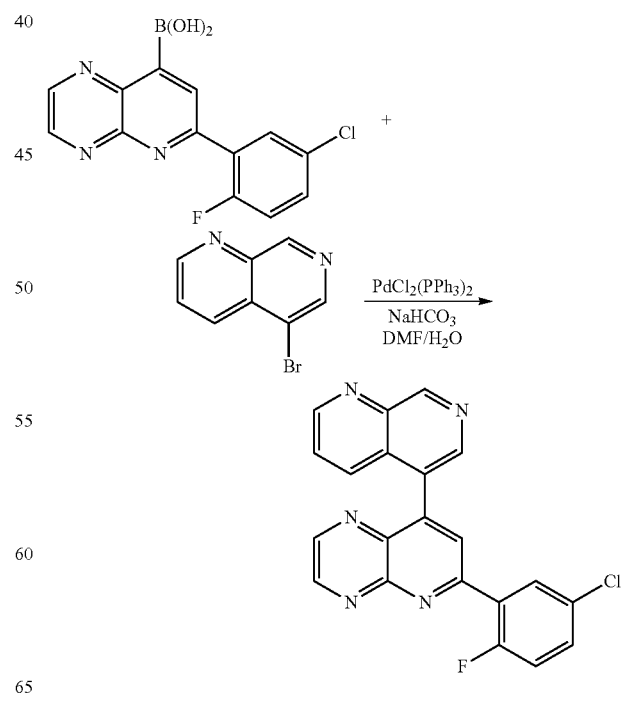

The synthesis can be performed as in example 1, step 5.

II. Assays

Example 9

In-Vitro (Enzyme) Assay for Determination of the Efficacy of Inhibitors of the Inhibition of TGF-Beta-Mediated Effects

The kinase assay was carried out as 384-well flashplate assay. 31.2 nM of GST-ALK5, 439 nM of GST-SMAD2 and 3 mM of ATP (with 0.3 µCi of $^{33}$P-ATP/well) were incubated in a total volume of 35 µl (20 mM of HEPES, 10 mM of $MgCl_2$, 5 mM of $MnCl_2$, 1 mM of DTT, 0.1% of BSA, pH 7.4) without or with test substance (5-10 concentrations) at 30° C. for 45 min. The reaction was stopped using 25 µl of 200 mM EDTA solution, filtered with suction at room temperature after 30 min, and the wells were washed with 3 times 100 µl of 0.9% NaCl solution. Radioactivity was measured in the TopCount. The $IC_{50}$ values were calculated using RS 1. The results are given in Table 2.

Example 10

Inhibition of Smad2/3 Phosphorylation in Mv1Lu Cells by TGF-Beta Receptor I Kinase Inhibitors

This assay was used to determine the inhibitory potency of compounds on TGF-beta-induced phosphorylation of Smad2 (Ser465/467) and Smad3 (Ser423/425). Mv1-Lu cells (lung epithelial cell line from mink *Mustela vison*; ATCC number: CCL-64) were seeded in DMEM (Invitrogen) supplemented with 10% fetal bovine serum (Pan Biotech) at a defined cell density in 24-well or 96-well plates (24-well plate: $1.5 \times 10^5$ cells per well; 96-well plate: $4 \times 10^4$ cells per well). Cell cultures were incubated in DMEM at 37° C. and 10% $CO_2$. On the next day, the medium was replaced and cells were serum-starved for 16-20 hours. The following day, serial dilutions of compounds were added to the wells, pre-incubated for 1.5 hrs before recombinant TGF-beta 1 ligand (final concentration 5 ng/ml; R&D systems) was added. After one hour of ligand stimulation, lysates were prepared and analyzed using an enzyme-linked immunosorbent assay kit (PathScan Phospho-Smad2 Kit, Cell Signaling Technologies). The ELISA detects phosphorylated Smad2 as well as phosphorylated Smad3 with the phospho-specific antibody. TGF-beta stimulated cells and unstimulated cells served as positive and negative controls (100% and background control). The concentration of the vehicle DMSO was kept constant at 0.2% (v/v) in all wells. Dose-response relationships were fitted using curve fitting algorithms of the RS1 statistics software package (Brooks Automation Inc. RS/1—Statistical Tools Handbook. Release 6.2) to determine the concentration at which half-maximal inhibition ($IC_{50}$) of Smad2/3 phosphorylation was achieved. The results are given in Table 2.

TABLE 2

| Compound | Structure | Name | HPLC/MS Rt. [min] | HPLC/MS [M + H] | TβR activity (Example 9) 0 >10 µM + 1-10 µM ++ <1 µM | TβR activity (Example 10) 0 >10 µM + 1-10 µM ++ <1 µM |
|---|---|---|---|---|---|---|
| 1 | 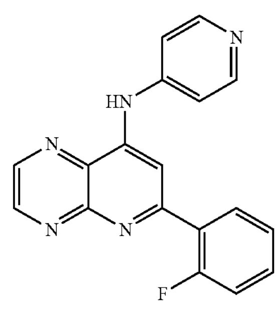 [SMILES: Fc1ccccc1-c1cc(Nc2ccncc2)c2nccnc2n1] | [6-(2-Fluorophenyl)-pyrido[2,3-b]pyrazin-8-yl]-pyridin-4-yl-amine | 1.37 (A) | 318 | ++ | ++ |
| 2 | 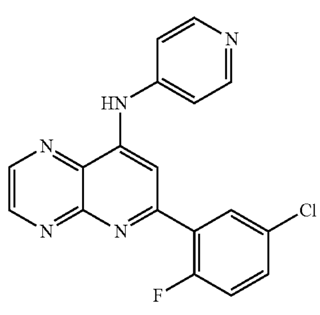 [SMILES: Fc1ccc(Cl)cc1-c1cc(Nc2ccncc2)c2nccnc2n1] | [6-(5-Chloro-2-fluoro-phenyl)-pyrido[2,3-b]pyrazin-8-yl]-pyridin-4-yl-amine | 1.55 (A) | 352 | ++ | ++ |

TABLE 2-continued

| Compound | Structure | Name | HPLC/ MS Rt. [min] | HPLC/ MS [M + H] | TβR activity (Example 9) 0 >10 μM + 1-10 μM ++ <1 μM | TβR activity (Example 10) 0 >10 μM + 1-10 μM ++ <1 μM |
|---|---|---|---|---|---|---|
| 3 | 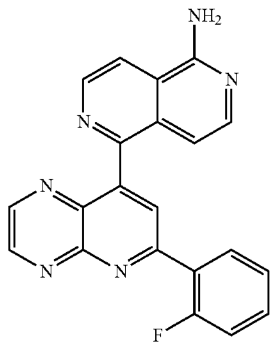 [SMILES: Nc1nccc2c(-c3cc(-c4ccccc4F)nc4nccnc34)nccc12] | 5-[6-(2-Fluorophenyl)-pyrido[2,3-b]pyrazin-8-yl]-[2,6]naphthyridin-1-ylamine | 1.45 (A) | 369 | ++ | ++ |
| 4 | 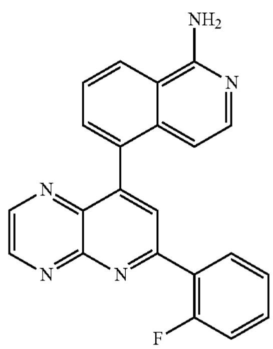 [SMILES: Nc1nccc2c(-c3cc(-c4ccccc4F)nc4nccnc34)cccc12] | 5-[6-(2-Fluorophenyl)-pyrido[2,3-b]pyrazin-8-yl]-isoquinolin-1-ylamine | 1.61 (A) | 368 | ++ | ++ |
| 5 | 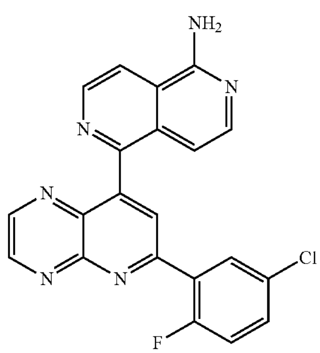 [SMILES: Nc1nccc2c(-c3cc(-c4cc(Cl)ccc4F)nc4nccnc34)nccc12] | 5-[6-(5-Chloro-2-fluorophenyl)-pyrido[2,3-b]pyrazin-8-yl]-[2,6]naphthyridin-1-ylamine | 1.72 (A) | 403 | | ++ |
| 6 | 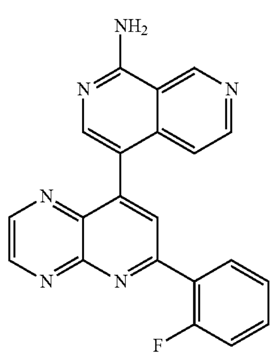 [SMILES: Nc1ncc(-c2cc(-c3ccccc3F)nc3nccnc23)c2ccncc12] | 4-[6-(2-Fluorophenyl)-pyrido[2,3-b]pyrazin-8-yl]-[2,7]naphthyridin-1-ylamine | 1.32 (A) | 369 | ++ | ++ |

TABLE 2-continued

| Compound | Structure | Name | HPLC/ MS Rt. [min] | HPLC/ MS [M + H] | TβR activity (Example 9) 0 >10 μM + 1-10 μM ++ <1 μM | TβR activity (Example 10) 0 >10 μM + 1-10 μM ++ <1 μM |
|---|---|---|---|---|---|---|
| 8 | 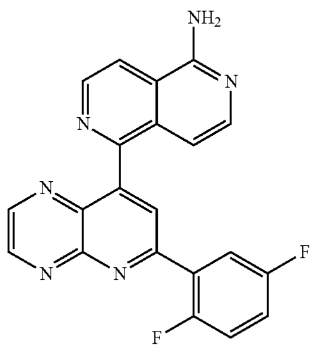 [SMILES: Nc1nccc2c(-c3cc(-c4cc(F)ccc4F)nc4nccnc34)nccc12] | 5-[6-(2,5-Difluoro-phenyl)pyrido[2,3-b]pyrazin-8-yl]-2,6-naphthyridin-1-amine | 1.67 (B) | 387 | | ++ |
| 9 | 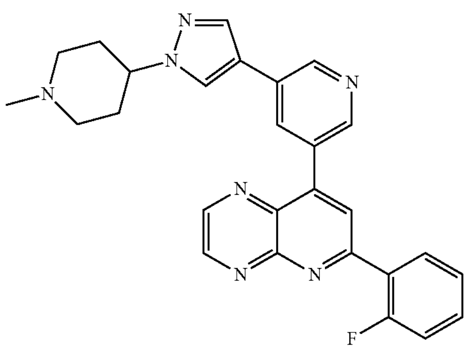 [SMILES: CN1CCC(n2cc(-c3cncc(-c4cc(-c5ccccc5F)nc5nccnc45)c3)cn2)CC1] | 6-(2-Fluorophenyl)-8-{5-[1-(1-methyl-piperidin-4-yl)-1H-pyrazol-4-yl]-pyridin-3-yl}-pyrido[2,3-b]pyrazine | 1.47 (A) | 466 | ++ | ++ |
| 10 | 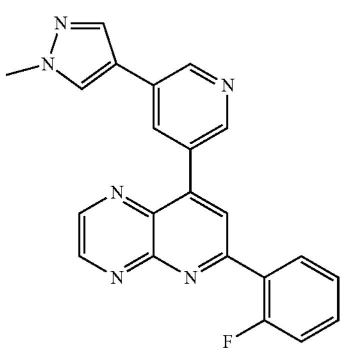 [SMILES: Cn1cc(-c2cncc(-c3cc(-c4ccccc4F)nc4nccnc34)c2)cn1] | 6-(2-Fluorophenyl)-8-[5-(1-methyl-1H-pyrazol-4-yl)-pyridin-3-yl]-pyrido[2,3-b]pyrazine | 2.27 (B) | 383 | ++ | ++ |
| 12 | 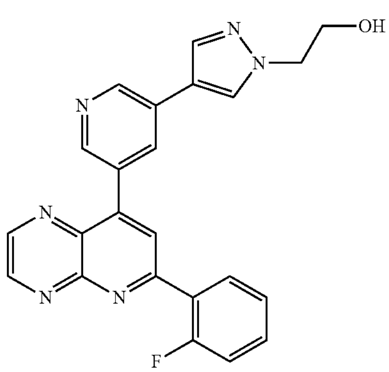 [SMILES: OCCn1cc(-c2cncc(-c3cc(-c4ccccc4F)nc4nccnc34)c2)cn1] | 2-[4-[5-[6-(2-Fluorophenyl)pyrido[2,3-b]pyrazin-8-yl]-3-pyridyl]pyrazol-1-yl]ethanol | 1.63 (A) | 413 | ++ | ++ |

TABLE 2-continued

| Compound | Structure | Name | HPLC/ MS Rt. [min] | HPLC/ MS [M + H] | TβR activity (Example 9) 0 >10 μM + 1-10 μM ++ <1 μM | TβR activity (Example 10) 0 >10 μM + 1-10 μM ++ <1 μM |
|---|---|---|---|---|---|---|
| 14 | 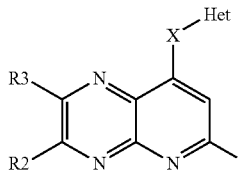 | N-[6-(5-Chloro-2-fluorophenyl)pyrido[2,3-b]pyrazin-8-yl]furo[3,2-b]pyridin-7-amine | 1.65 (A) | 392 | ++ | ++ |

The invention claimed is:

1. A compound of formula (I)

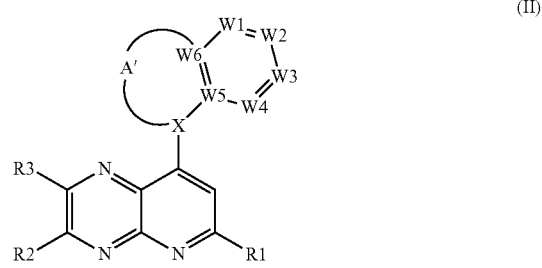

(I)

wherein:

X denotes absent, NR4 or CR5R6;

R1 denotes monocyclic aryl having 3, 4, 5, 6, 7 or 8 C atoms or a monocyclic heteroaryl having 1, 2, 3, 4, 5, 6, 7 or 8 C atoms and 1, 2, 3, 4 or 5 N, O and/or S atoms, each of which can independently from each other be substituted by at least one substituent selected from the group consisting of Y, Hal, CN, CF$_3$ and OY;

R2 denotes H, A, —OY, —NH$_2$ or —NAA;

R3 denotes H, A, —OY or —NYY;

R4, R5 and R6 independently from each other denote absent, H or A;

R7 denotes Hal, A, —(CYY)$_n$—OY, —(CYY)$_n$—NYY, (CYY)$_n$-Het$^2$, (CYY)$_n$—O-Het$^2$, SY, NO$_2$, CN, COOY, —CO—NYY, —NY—COA, —NY—SO$_2$A, —SO$_2$—NYY, S(O)$_m$A, —CO-Het$^2$, —O(CYY)$_n$—NYY, —O(CYY)$_n$-Het$^2$, —NH—COOA, —NH—COO—(CYY)$_n$—NYY, —NH—COO—(CYY)$_n$-Het$^2$, —NH—CO—NH—(CYY)$_n$—NYY, —NH—CO—NH(CYY)$_n$-Het$^2$, —OCO—NH—(CYY)$_n$—NYY, —OCO—NH—(CYY)$_n$-Het$^2$, CHO, COA, =S, =NY or =O;

Y denotes H or A;

A denotes unbranched or branched alkyl having 1, 2, 3, 4, 5, 6, 7, 8, 9 or 10 C atoms, wherein 1, 2, 3, 4, 5, 6 or 7 H atoms can be replaced independently from one another by Hal and/or wherein one or two CH$_2$ groups can be replaced independently of one another by O, S, SO, SO$_2$, a —CY=CY— group and/or a —C≡C— group, or denotes cyclic alkyl with 3, 4, 5, 6 or 7 C atoms;

Het denotes a saturated or unsaturated, monocyclic, bicyclic or tricyclic heterocycle having 3, 4, 5, 6, 7, 8, 9, 10, 11, 12, 13, 14, 15, 16, 17, 18, 19 or 20 C atoms and 1, 2, 3, 4 or 5 N, O and/or S atoms, which can independently from each other be substituted by at least one substituent R7;

Het$^2$ denotes a saturated or unsaturated, monocyclic, bicyclic or tricyclic heterocycle having 3, 4, 5, 6, 7, 8, 9, 10, 11, 12, 13, 14, 15, 16, 17, 18, 19 or 20 C atoms and 1, 2, 3, 4 or 5 N, O and/or S atoms, which can independently from each other be substituted by at least one substituent selected from the group consisting of Hal, A, —(CYY)$_n$—OY, —(CYY)$_n$—NYY, (CYY)$_n$-Het$^3$, (CYY)$_n$—O-Het$^3$, SY, NO$_2$, CN, COOY, —CO—NYY, —NY—COA, —NY—SO$_2$A, —SO$_2$—NYY, S(O)$_m$A, —CO-Het$^3$, —O(CYY)$_n$—NYY, —O(CYY)$_n$-Het$^3$, —NH—COOA, —NH—CO—NYY, —NH—COO—(CYY)$_n$—NYY, —NH—COO—(CYY)$_n$-Het$^3$, —NH—CO—NH—(CYY)$_n$—NYY, —NH—CO—NH(CYY)$_n$-Het$^3$, —OCO—NH—(CYY)$_n$—NYY, —OCO—NH—(CYY)$_n$-Het$^3$, CHO, COA, =S, =NY and =O;

Het$^3$ denotes a saturated or unsaturated, monocyclic, bicyclic or tricyclic heterocycle having 3, 4, 5, 6, 7, 8, 9, 10, 11, 12, 13, 14, 15, 16, 17, 18, 19 or 20 C atoms and 1, 2, 3, 4 or 5 N, O and/or S atoms, which can independently from each other be substituted by at least one substituent selected from the group consisting of Hal, A, —(CYY)$_n$—OY, —(CYY)$_n$—NYY, SY, NO$_2$, CN, COOY, —CO—NYY, —NY—COA, —NY—SO$_2$A, —SO$_2$—NYY, S(O)$_m$A, —NH—CODA, —NH—CO—NYY, CHO, COA, =S, =NY and =O;

Hal denotes F, Cl, Br or I;

m denotes 0, 1, or 2;

n denotes 0, 1, 2, 3 or 4;

or a physiologically acceptable salt, tautomer or stereoisomer thereof, including mixtures thereof in all ratios.

2. A compound of formula (II) according to claim 1, (II)

wherein:

A' denotes absent or together with X, W5 and W6 denotes monocyclic or bicyclic aryl having 3, 4, 5, 6, 7, 8, 9 or 10

C atoms, each of which can independently from each other be substituted by at least one substituent R7, or together with X, W5 and W6 denotes Het;

X denotes absent, NR4 or CR5R6 or together with A', W5 and W6 denotes monocyclic or bicyclic aryl having 3, 4, 5, 6, 7, 8, 9 or 10 C atoms, each of which can independently from each other be substituted by at least one substituent R7, or together with A', W5 and W6 denotes Het; with the first proviso that, if X is absent, A' is also absent and W5 is directly linked to the pyrido[2,3-b]pyrazine moiety;

W, W2, W3, W4 and W6 independently from each other denote N or CR8, with the proviso that at least one of W1, W2, W3, W4 and W6 is N and, when A' together with X, W5 and W6 denotes monocyclic or bicyclic aryl having 3, 4, 5, 6, 7, 8, 9 or 10 C atoms, then W6 is C and one of W1, W2, W3 and W4 is N;

W5 is C;

R8 denotes absent, H, A, —OY, —NYY, —NY—COY or Het$^2$;

or a physiologically acceptable salt, tautomer or stereoisomer thereof, including mixtures thereof in all ratios.

3. A compound according to claim 2, wherein X denotes NR4 or CR5R6 and A' is absent;

or a physiologically acceptable salt, tautomer or stereoisomer thereof, including mixtures thereof in all ratios.

4. A compound according to claim 2, wherein X and A' are both absent and W5 is directly linked to the pyrido[2,3-b]pyrazine moiety or X together with A',W5 and W6 denotes monocyclic or bicyclic aryl having 3, 4, 5, 6, 7, 8, 9 or 10 C atoms, each of which can independently from each other be substituted by at least one substituent R7;

or a physiologically acceptable salt, tautomer or stereoisomer thereof, including mixtures thereof in all ratios.

5. A compound according to claim 2, wherein

X is absent or denotes NR4, wherein if X is absent, A' is also absent and W5 is directly linked to the pyrido[2,3-b]pyrazine moiety; or X, A', W5 and W6 together denote monocyclic aryl having 5 or 6 C atoms, each of which can independently from each other be substituted by at least one substituent R7, or together denote Het;

Het denotes a saturated or unsaturated, monocyclic or bicyclic heterocycle having 3, 4, 5, 6, 7, 8 or 9 C atoms and 1 or 2 N atoms, which can independently from each other be substituted by at least one substituent R7;

Het$^2$ denotes a saturated or unsaturated, monocyclic or bicyclic heterocycle having 3, 4, 5, 6, 7, 8 or 9 C atoms and 1 or 2 N atoms, which can independently from each other be substituted by at least one substituent selected from the group consisting of Hal, A, —(CYY)$_n$—OY and —(CYY)$_n$-Het$^3$;

Het$^3$ denotes a saturated or unsaturated, monocyclic or bicyclic heterocycle having 3, 4, 5, 6, 7, 8 or 9 C atoms and 1 or 2 N atoms, which can independently from each other be substituted by at least one substituent selected from Hal or A;

R1 denotes monocyclic aryl having 5 or 6 C atoms which can be substituted by at least one substituent selected from the group consisting of Y, Hal, CN, CF$_3$ and OY;

R2, R3 and R4 independently from each other denote H or A;

R7 denotes A, —(CYY)$_n$—NYY or —(CYY)$_n$-Het$^2$;

R8 denotes absent, H, A, —NYY or Het$^2$;

Y denotes H or A;

A denotes unbranched or branched alkyl having 1, 2, 3, 4, 5, 6, 7 or 8 C atoms;

Hal denotes F or Cl; and n is 0, 1 or 2;

or a physiologically acceptable salt, tautomer or stereoisomer thereof, including mixtures thereof in all ratios.

6. A compound according to claim 1, wherein X denotes NR4 or CR5R6 or a physiologically acceptable salt, tautomer or stereoisomer thereof, including mixtures thereof in all ratios.

7. A compound according to claim 1, wherein X is absent;

or a physiologically acceptable salt, tautomer or stereoisomer thereof, including mixtures thereof in all ratios.

8. A compound according to claim 1, wherein Het is selected from the group consisting of: pyridinyl, naphthyridinyl, isoquinolinyl, pyrrolopyridinyl, and furopyridinyl;

or a physiologically acceptable salt, tautomer or stereoisomer thereof, including mixtures thereof in all ratios.

9. A compound according to claim 1, wherein

X is absent or denotes NR4

Het denotes a saturated or unsaturated, monocyclic or bicyclic heterocycle having 3, 4, 5, 6, 7, 8 or 9 C atoms and 1 or 2 N atoms, which can independently from each other be substituted by at least one substituent R7;

Het$^2$ denotes a saturated or unsaturated, monocyclic or bicyclic heterocycle having 3, 4, 5, 6, 7, 8 or 9 C atoms and 1 or 2 N atoms, which can independently from each other be substituted by at least one substituent selected from the group consisting of Hal, A, —(CYY)$_n$—OY and —(CYY)$_n$-Het$^3$; and Het$^3$ denotes a saturated or unsaturated, monocyclic or bicyclic heterocycle having 3, 4, 5, 6, 7, 8 or 9 C atoms and 1 or 2 N atoms, which can independently from each other be substituted by at least one substituent selected Hal or A;

R1 denotes monocyclic aryl having 5 or 6 C atoms which can be substituted by at least one substituent selected from the group consisting of Y, Hal, CN, CF$_3$ and OY;

R2, R3 and R4 independently from each other denote H or A;

R7 denotes A, —(CYY)$_n$—NYY or —(CYY)$_n$-Het$^2$;

Y denotes H or A;

A denotes unbranched or branched alkyl having 1, 2, 3, 4, 5, 6, 7 or 8 C atoms;

Hal denotes F or Cl; and n is 0, 1 or 2;

or a physiologically acceptable salt, tautomer or stereoisomer thereof, including mixtures thereof in all ratios.

10. A compound according to claim 1, wherein X denotes NR4, or a physiologically acceptable salt, tautomer or stereoisomer thereof, including mixtures thereof in all ratios.

11. A compound according to claim 1, wherein Het is selected from the group consisting of: pyridin-3-yl, pyridin-4-yl, [2,7]naphthyridin-1-yl, [3,7]naphthyridin-1-yl, [2,6]naphthyridin-1-yl, isoquinolin-1-yl, pyrrolo[3,2-c]pyridin-1-yl, and furo[3,2-b]pyridin-7-yl;

or a physiologically acceptable salt, tautomer or stereoisomer thereof, including mixtures thereof in all ratios.

12. A compound according to claim 1, which is selected from the group consisting of:
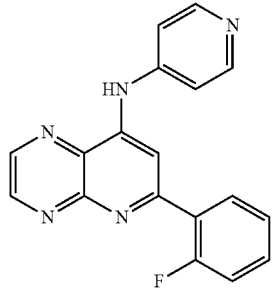
Compound 1
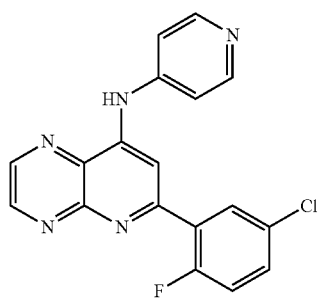
Compound 2
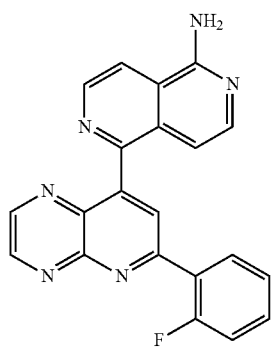
Compound 3
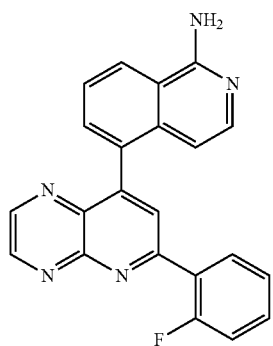
Compound 4
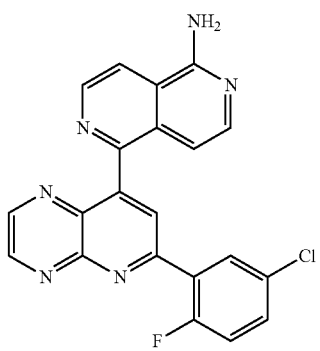
Compound 5
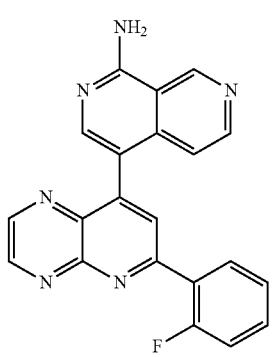
Compound 6
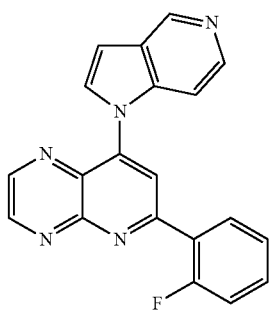
Compound 7
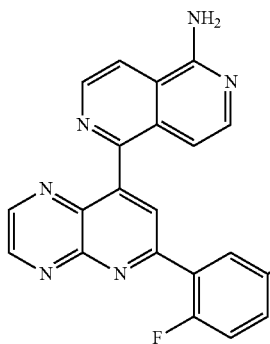
Compound 8

-continued

Compound 9

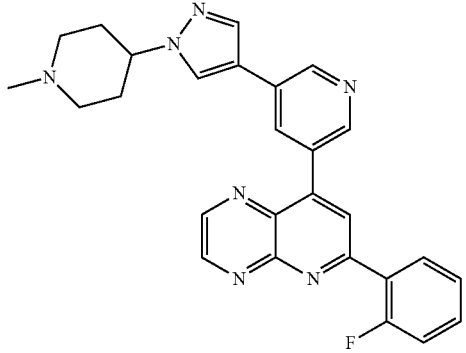

Compound 10

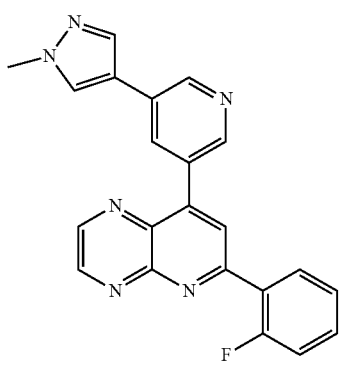

Compound 11

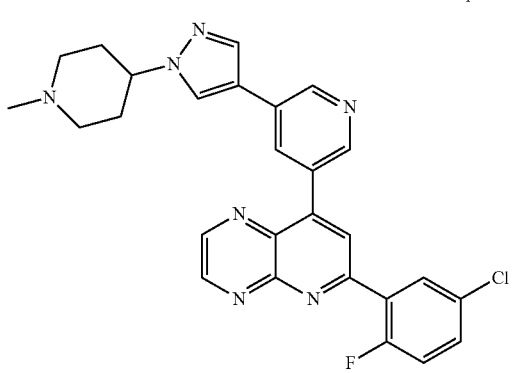

Compound 12

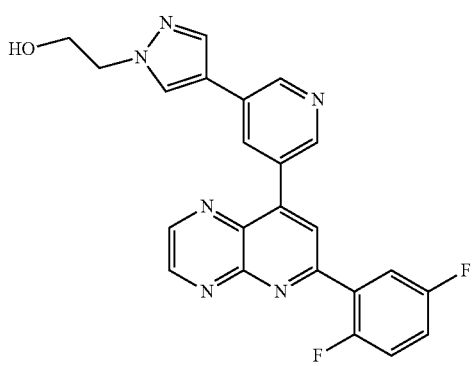

-continued

Compound 13

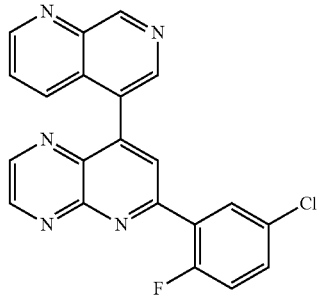

Compound 14

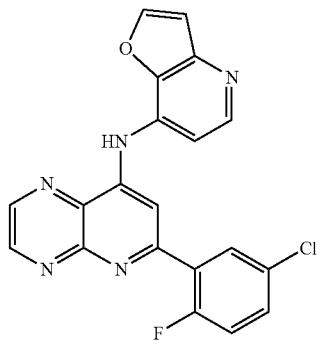 [SMILES: Fc1ccc(Cl)cc1-c1cc(Nc2ccnc3ccoc23)c2nccnc2n1]

or a physiologically acceptable salt, tautomer or stereoisomer thereof, including mixtures thereof in all ratios.

13. A medicament composition comprising at least one compound according to claim 1 and a pharmaceutically acceptable carrier.

14. The medicament composition according to claim 13, wherein such medicament composition comprises at least one additional pharmacologically active substance.

15. The medicament composition according claim 13, wherein the medicament composition is applied before and/or during and/or after treatment with at least one additional pharmacologically active substance.

16. A pharmaceutical composition comprising a therapeutically effective amount of at least one compound according to claim 1, and further comprising at least one additional compound selected from the group consisting of physiologically acceptable excipients, auxiliaries, adjuvants, diluents, and carriers.

17. A kit comprising a therapeutically effective amount of at least one compound according to claim 1 and a therapeutically effective amount of at least one further pharmacologically active substance other than the compound according to claim 1.

18. A method for inhibiting transforming growth factor-beta receptor kinase, recepteur d'origine Nantais kinase, tat-associated kinase 1, protein kinase 1, misshapen-like kinase 1, stress activated protein kinase 2-alpha, stress activated protein kinase 2-beta or checkpoint kinase 2, in a mammal, comprising contacting the protein with a compound of claim 1.

19. A process for manufacturing a compound of formula (I) according to claim 1, comprising the steps of:
(a) reacting a compound of formula (III)

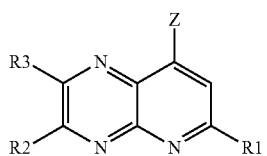

(III)

wherein
Z denotes Hal or B(OH)$_2$,
with a compound of formula (IVa) or formula (IVb)
H—X-Het (IVa)
Z'-Het (IVb)
wherein
Z' denotes Hal, boronic acid or an ester of boronic acid,
to yield the compound of formula (I)
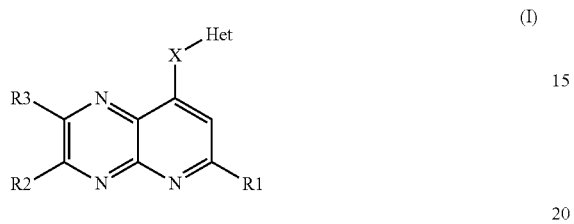
(I)
and optionally
(b) converting a base or an acid of the compound of formula (I), into a physiologically acceptable salt thereof.
\* \* \* \* \*